US010257296B2

(12) United States Patent
Uchida et al.

(10) Patent No.: US 10,257,296 B2
(45) Date of Patent: Apr. 9, 2019

(54) SERVICE PROVIDING SYSTEM, SERVICE PROVIDING DEVICE, AND DATA CONSTRUCTING METHOD

(71) Applicants: KABUSHIKI KAISHA TOSHIBA, Minato-ku (JP); TOSHIBA DIGITAL SOLUTIONS CORPORATION, Kawasaki-shi (JP)

(72) Inventors: Satoshi Uchida, Meguro (JP); Junta Asano, Fuchu (JP); Hideto Shimizu, Ota (JP); Hidehiro Tochimoto, Saitama (JP); Hisao Kawasato, Kawasaki (JP)

(73) Assignees: KABUSHIKI KAISHA TOSHIBA, Minato-ku (JP); Toshiba Digital Solutions Corporation, Kawasaki-shi (JP)

( * ) Notice: Subject to any disclaimer, the term of this patent is extended or adjusted under 35 U.S.C. 154(b) by 0 days.

(21) Appl. No.: 15/556,687

(22) PCT Filed: Mar. 8, 2016

(86) PCT No.: PCT/JP2016/057250
§ 371 (c)(1),
(2) Date: Sep. 8, 2017

(87) PCT Pub. No.: WO2016/143800
PCT Pub. Date: Sep. 15, 2016

(65) Prior Publication Data
US 2018/0109637 A1    Apr. 19, 2018

(30) Foreign Application Priority Data

Mar. 9, 2015 (JP) ................................. 2015-046206
Jun. 3, 2015 (JP) ................................. 2015-113507

(51) Int. Cl.
*G06Q 50/10* (2012.01)
*H04L 29/08* (2006.01)
(Continued)

(52) U.S. Cl.
CPC ............. *H04L 67/22* (2013.01); *G06Q 10/10* (2013.01); *G06Q 50/10* (2013.01); *G08B 5/36* (2013.01);
(Continued)

(58) Field of Classification Search
CPC .......... G06Q 50/10; G06Q 50/12; G08B 5/24; G08B 5/32; G08B 5/36; G08B 5/38; H04L 67/22; H04L 67/26; H04L 67/1097
See application file for complete search history.

(56) References Cited

U.S. PATENT DOCUMENTS

| 2004/0101178 A1* | 5/2004 | Fedorovskaya ....... G06F 19/321 382/128 |
| 2007/0165812 A1 | 7/2007 | Lee et al. |
| 2013/0279631 A1* | 10/2013 | Bowers ................... H04L 27/04 375/300 |

FOREIGN PATENT DOCUMENTS

| CN | 1514399 A | 7/2004 |
| JP | 2002-083215 A | 3/2002 |

(Continued)

OTHER PUBLICATIONS

International Search Report dated Jun. 14, 2016 in PCT/JP2016/057250, filed on Mar. 8, 2016.

*Primary Examiner* — Van T Trieu
(74) *Attorney, Agent, or Firm* — Oblon, McClelland, Maier & Neustadt, L.L.P.

(57) ABSTRACT

According to one embodiment, a service providing system accumulates, as first context information linked to identification information of a first user, at least a part of first data detected by a first sensor worn on a body of the first user or (Continued)

provided in a held object of the first user. The service providing system provides a first service based on a first aggregate of the accumulated first context information to the first user.

18 Claims, 8 Drawing Sheets

(51) Int. Cl.
*G08B 5/36* (2006.01)
*G06Q 10/10* (2012.01)
*G06Q 50/12* (2012.01)
*G06Q 50/00* (2012.01)

(52) U.S. Cl.
CPC ............ *H04L 67/26* (2013.01); *G06Q 50/01* (2013.01); *G06Q 50/12* (2013.01)

(56) References Cited

FOREIGN PATENT DOCUMENTS

| | | | |
|---|---|---|---|
| JP | 2005-031916 A | 2/2005 |
| JP | 2006-059094 A | 3/2006 |
| JP | 2007-195148 A | 8/2007 |
| JP | 2009-211578 A | 9/2009 |
| JP | 2013-050824 A | 3/2013 |
| JP | 2014-211677 A | 11/2014 |
| WO | 2013/084742 A1 | 6/2013 |

\* cited by examiner

SERVICE PROVIDING SYSTEM, SERVICE PROVIDING DEVICE, AND DATA CONSTRUCTING METHOD

TECHNICAL FIELD

Embodiments of the invention relate to a service providing system, service providing device, and a data constructing method.

BACKGROUND ART

There is a service providing system (a network system) that provides a service including information to users. It is desired to provide more enjoyment.

CITATION LIST

Patent Literature

PTL 1: JP-A-2013-50824 (Kokai)
PTL 2: JP-A-2014-211677 (Kokai)

SUMMARY OF INVENTION

Technical Problem

Embodiments of the invention provide service providing systems, service providing devices, and data constructing methods that can provide more enjoyment.

Solution to Problem

According to an embodiment of the invention, a service providing system accumulates, as first context information linked to identification information of a first user, at least a part of first data detected by a first sensor worn on the body of the first user or provided in a held object of the first user. The service providing system provides a first service based on a first aggregate of the accumulated first context information to the first user.

DESCRIPTION OF EMBODIMENTS

Figure 1:
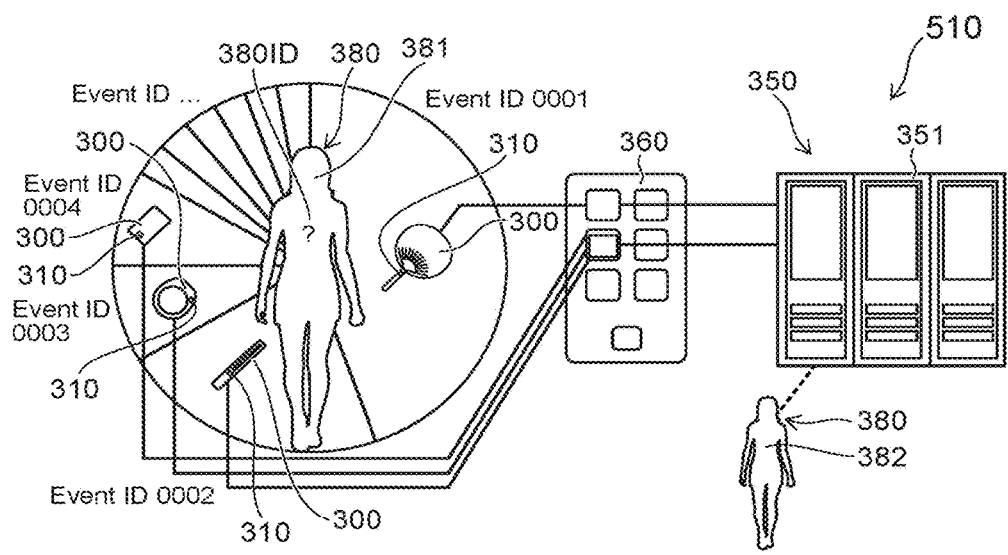
FIG. 1 is a schematic diagram illustrating a service providing system according to a first embodiment.

Embodiments of the invention are explained below with reference to the drawings.

Note that, in the figures in this specification, the same elements as elements described with reference to the figures already referred to are denoted by the same reference numerals and signs and detailed explanation of the elements is omitted.

First Embodiment

FIG. 1 is a schematic diagram illustrating a service providing system according to a first embodiment.

As shown in FIG. 1, in a service providing system 510 according to the first embodiment, data concerning a user 380 (e.g., a first user 381) is collected by a sensing device 310.

The sending device 310 is provided in, for example, goods 300 held by the user 380. The sensing device 310 may be worn on the body of the user 310. The sensing device 310 may be provided in a held object (the goods 300) held by the user 310. The held object is used for, for example, cheering of an event. As explained below, the held object includes at least any one of a light emitting device, a flag-like body, a fan-like body, a cloth-like body, a megaphone, a microphone, a bracelet, a necklace, a watch, a finger ring, eyeglasses, clothes, a shoe, a glove, a cap, a headphone, an earphone, a hearing aid, an accessory, and a sporting instrument.

The sensing device 310 is, for example, a sensor. The sensing device 310 detects, for example, a state of the body of the user 380. The state of the body of the user 380 includes a movement of the body of the user 380 (e.g., movements of hands, feet, and the like), a posture of the body, voice, a line of sight, a blood pressure, and a pulse. The state detected by the sensing device 310 may be related to an action of the user 380. The sensing device 310 may detect, for example, movements of the goods 300 associated with the movement of the body of the user 380. Information concerning the states detected by the sensing device 310 is provided to a cloud 350. For example, detected data is provided to, for example, a cloud server 351 of the cloud 350 via management application software 360.

For example, a service is provided to the user 380 on the basis of the information provided to the cloud server 351. The service may be performed on the basis of a characteristic (e.g., a taste) of the user 380. The characteristic (the taste) of the user 380 is estimated from, for example, the state of the user 380 detected by the sensing device 310.

In the embodiment, when the sensing device 310 detects the state of the body of the user 380, the user 380 may participate in an event. For example, the user 380 participates in a plurality of events. For example, event IDs (0001, etc.) may be provided in the respective plurality of events. For example, data concerning the respective events of the user 380 are acquired and accumulated. For example, the user 380 carries the goods 300 provided with the sensing device 310 and participates in the event. States of the user 380 in the event are detected by the sensing device 310. The user 380 is a supporter of a performer 385 who appears in the event.

In the first embodiment, a "persona" (e.g., a nickname) is provided to correspond to the user 380. "Personas" are provided in association with a respective plurality of users 380. For example, the "persona" may not include personal information of the user 380. By using the "persona", data concerning the characteristic of the user 380 is provided to the cloud server 351 without involving the personal information of the user 380.

As explained above, a first sensor (the sensing device 310) is worn on the body of the user 380 (the first user 381). The first sensor is provided in the held object (the goods 300, etc.) of the user 380 (the first user 381). At least a part of first data detected by the first sensor is accumulated. The accumulation is performed by, for example, a server. The server is, for example, the cloud server 351. The data is accumulated as first context information linked to identification information of the user 380 (the first user 381). In the accumulation, for example, a "persona" linked to the identification information of the user 380 is used. For example, the first context information includes information concerning a characteristic (e.g., a taste) of the first user 381.

For example, the user 380 can specify the goods 300 held by the user 380. On the other hand, others (e.g., a second user 382) excluding the user 380 may not be able to specify a person holding the goods 300.

Data (e.g., the first context information) concerning the characteristic (e.g., the taste) of the user 380 (e.g., the first user 381) is accumulated, for example, without involving personal information. For example, in the cloud server 351, data concerning characteristics (tastes) of the respective plurality of users 380 are accumulated without specifying, for example, personal information. A "persona", in which the data concerning the characteristic (the taste) of a fan (the user 380) is accumulated, is generated on a platform.

A first service based on a first aggregate (e.g., the "persona") of the accumulated first context information is provided to the user 380 (the first user 381). For example, the first aggregate (e.g., the "persona") of the first context information includes a plurality of kinds of first context information. A characteristic (e.g., a taste) of the first user 381 is estimated on the basis of the first aggregate of the accumulated plurality of kinds of first context information. The first service is decided on the basis of the estimated characteristic (taste) of the first user 381. The first service is provided to the first user 381.

The first service based on the characteristic (e.g., the taste) estimated from the first aggregate of the accumulated plurality of kinds of first context information is provided. Therefore, the first service can provide more enjoyment to the first user 381.

As explained above, in the embodiment, the first data concerning the first user 381 detected by the first sensor of the first user 381 is accumulated as the first context information linked to the identification information. The first context information corresponds to experience information of the first user 381. For example, the "persona" is formed as the first aggregate of the first context information. The first service based on the first aggregate (e.g., the "persona") is provided to the first user 381. The first service affects experience of the first user 381.

Further, in the first embodiment, a second service based on the first data concerning the first user 381 detected by the sensing device 310 may be provided to another user 380 (the second user 382) from the cloud server 351.

For example, the second user 382 has a characteristic (e.g., a taste) similar to the characteristic (e.g., the taste) of the first user 381. For example, the characteristic (e.g., the taste) of the first user 381 and the characteristic (e.g., the taste) of the second user 382 have similarities to each other. The first user 381 and the second user 382 belong to, for example, the same community. Information concerning the first user 381 is provided to the second user 382 belonging to the same community.

For example, a characteristic (e.g., a taste) of the second user 382 is estimated in the same manner as the estimation of the characteristic (e.g., the taste) of the first user 381. For example, concerning the second user 382, a "persona" of the second user 382 is created in the same manner as the creation of the "persona" concerning the first user 381. For example, a second sensor is worn on the body of the second user 382. The second sensor is provided in a held object of the second user 382. At least a part of a plurality of second data detected by the second sensor is accumulated as a plurality of kinds of second context information linked to identification information of the second user 382. The accumulation is performed in, for example, the cloud server 351. A characteristic (e.g., a taste) of the second user 382 is estimated on the basis of a second aggregate of the accumulated plurality of kinds of second context information (the "persona" of the second user 382). When a difference between the estimated characteristic (e.g., taste) of the second user 382 and the estimated characteristic (e.g., taste) of the first user 381 is smaller than a standard, a second service based on at least a part of the first data is provided to the second user 382.

For example, data on which characteristics peculiar to a specific community are reflected is accumulated in the cloud server 351. The specific community includes the plurality of users 380. The user 380 who uses the cloud server 351 can perform more enjoyable information exchange, for example, in a community matching the characteristic of the user 380.

In the first embodiment, the data concerning the first user 381 detected by the sensing device 310 is provided to the second user 382, for example, without involving personal information of the first user 381.

On the other hand, in an information exchange method of a reference example, data including personal information is registered. In this case, since an individual is specified, a problem of infringement of privacy easily occurs. The occurrence of the problem can be suppressed by providing data not involving personal information. Consequently, security of the user 380 in the service providing system 510 according to the first embodiment is improved. Users of the service providing system increase.

In the embodiment, for example, the data concerning the first user 381 detected by the sensing device 310 is provided to the cloud server 351 without involving the personal information of the first user 381 and accumulated in the cloud server 351. Alternatively, the data concerning the first user 381 detected by the sensing device 310 may be provided to the cloud server 351 while involving the personal information of the first user 381 and accumulated in the cloud server 351. However, when at least a part of information concerning the first user 381 is provided to the second user 382, the personal information of the first user 381 is not provided to the second user 382.

In the first embodiment, it is possible to generate a user image closer to the characteristic of the user 380 without acquiring the personal information of the user 380 (e.g., a participant in an event). The user 380 can express the user 380 himself or herself in a combination of event IDs.

In the first embodiment, a deep emotion experience UX (User Experience) of the user 380 is detected by the sensing device 310. Data concerning the deep emotion experience UX is provided to, for example, the cloud server 351 of the cloud 350. An example of the deep emotion experience UX in the first embodiment is explained below.

Figure 2:
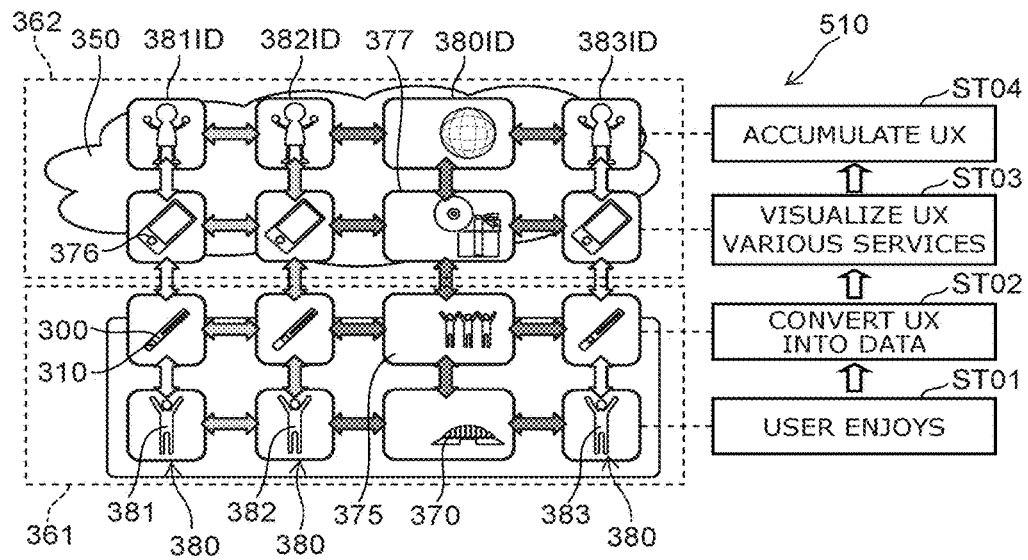
FIG. 2 is a schematic diagram illustrating the service providing system according to the first embodiment.

FIG. 2 is a schematic diagram illustrating the service providing system according to the first embodiment.

As shown in FIG. 2, in the first embodiment, a real UX 361 and a virtual UX 362 are provided. The real UX 361 includes, for example, the plurality of users 380 (first to third users 381 to 383) and a provider 370. The provider 370 provides information (which may include a service) to the plurality of users 380. Each of the plurality of users 380 enjoys, for example, an event (step ST01).

During the event, states of the respective users 380 are detected by the goods 300 including the sensing device 310. That is, the deep emotion experience UX is converted into data (step ST02). The detected states form at least a part of the deep emotion experience UX. The goods 300 including the sensing device 310 correspond to Things (T). During the event, a special thing 375 may be provided to the user 380. The provision of the special thing 375 may be performed on the basis of data of the deep emotion experience UX detected by the sensing device 310 during the event.

For example, the data concerning the detected deep emotion experience UX is provided to the cloud 350 of the virtual UX 362. For example, the deep emotion experience UX of each of the users 380 is visualized and provided to each of the users 380. Further, various services corresponding to the deep emotion experience UX of each of the users 380 are provided to each of the users 380. That is, step ST03 is carried out. In this case, application software 376 peculiar to the service providing system according to the first embodiment may be used. The application software 376 is provided, for example, from the provider 370 to each of the users 380. Special application software 377 corresponding to the deep emotion experience UX of each of the users 380 may be provided. For example, the special application software 377 may include a release key for encrypted data.

"Persona IDs 380ID" (first to third IDs 381ID to 383ID, etc.) corresponding to the respective plurality of users 380 are generated on the cloud 350. The deep emotion experiences UX of the respective plurality of users 380 are accumulated to correspond to the persona IDs 380ID (step ST04).

In this way, in the first embodiment, the deep emotion experience UX is grasped by the sensing device 310 (Things (T)). A plurality of deep emotion experiences UX are joined by the cloud 350.

As explained above, the service providing system 510 according to the first embodiment uses the sensing device 310 and a computer included in the cloud 350. In the cloud 350, a social network service is utilized. The service providing system 510 provides a high-context social network service, in which the sensing device 310 is utilized, to the user 380.

The plurality of users 380 having similar or the same characteristics (e.g., tastes) are included in one community. The plurality of users 380 included in the one community have, for example, similar or the same hobbies. The plurality of users 380 included in the one community have, for example, the similar or the same characteristics (e.g., tastes). The plurality of users 380 included in the one community have, for example, similar or the same senses of value.

Information peculiar to the user 380 is acquired by the sensing device 310. The information peculiar to the user 380 is peculiar to a community to which the user 380 belongs.

The sensing device 310 is provided in, for example, an article (the goods 300) peculiar to the community. Information peculiar to the community is acquired by the sensing device 310. The user can exchange information, for example, while using the information (data) peculiar to the community. For example, the plurality of users 380 may talk via a social network service.

It is enjoyable for the plurality of users 380 having the same hobby to exchange information (talk) concerning a certain theme. The theme is a theme peculiar to the hobby. Enjoyment is not sufficient, for example, even if a person talks about the theme with a person having a different hobby. Exchange of information concerning a theme peculiar to a hobby among a plurality of users having the same hobby leads to enjoyment. At this point, even if the respective plurality of users cannot be specified, the information exchange leads to enjoyment.

For example, there is a situation in which one user 380 (the first user 381) "achieves hole-in-one in golf". In the social network service of the reference example, the user provides a commemorative photograph or video to a network together with a comment. Other users provide comments in response to the commemorative photograph or video and the comment. In the reference example, the information exchange (communication) ends at this stage.

The first embodiment enables information exchange in an example explained below. In the situation in which "hole-in-one is achieved in golf", data detected by the sensing device 310 is provided to the cloud 350 (the social network service). For example, the sensing device 310 is provided in a club (a held object) of golf. The sensing device 310 acquires data concerning a swing of the club of golf. The sensing device 310 may acquire data concerning a wind direction and the like. Such data is "deep emotion experience data". The "deep emotion experience data" can be compared, for example, among the plurality of users 380.

For example, in the plurality of users 380 who enjoy golf as a hobby, the "deep emotion experience data" is understood in common. The plurality of users 380 have the same characteristic (e.g., taste) that the users can understand meaning of the data. The plurality of users 380 are included in one community. Another one (the second user 382) among the plurality of users 380 can provide (transmit) information concerning the "deep emotion experience data". The other (the second user 382) can transmit information indicating that, for example, "In such a situation? My previous swing was like this. Others' swings were like this." The situation in which "the hole-in-one is achieved in golf" develops into deeper communication through the "deep emotion experience data". This situation leads to deeper sympathy.

As explained above, content of the information exchange is shallow in the reference example. The information exchange is limited to thin conversation in the reference example. The information exchange leads to wide and thin conversation in the reference example. Therefore, it is difficult to obtain sufficient enjoyment.

On the other hand, in the first embodiment, content of the information exchange is deep. For example, the number of the plurality of users 380 having the similar or the same characteristics (e.g., tastes) may be small. However, the information exchange with deep content is possible. For example, narrow and dense conversation is possible. For example, people having the same sense of value can enjoy dense conversation. According to the first embodiment, unprecedented enjoyment is obtained. Enjoyment is further improved than in the past.

The first embodiment focuses on enjoyment in the user 380. The first embodiment focuses on the fact that, when the plurality of users 380 having "the similar or the same characteristics (e.g., tastes)" exchange information concerning the characteristics (e.g., the tastes), the information exchange leads to improvement of enjoyment.

In the example explained above according to the first embodiment, a common hobby is golf among the plurality of users 380 having the similar or the same characteristics (e.g., tastes). In the first embodiment, a type of a hobby is optional. For example, the characteristics (e.g., the tastes) include sports (e.g., snowboard), a concert, an amusement park (a theme park), a game, a toy, a meal, travel, a school festival, or a wedding ceremony.

For example, a specific performer appears in a concert. The user 380 may be, for example, a fan of the specific performer. The concert may include a plurality of gatherings held in different places or at different date and time. The specific performer appears in the plurality of gatherings. The specific performer is "the similar or the same characteristics (e.g., tastes)" in the plurality of users 380. Alternatively, another performer similar to the specific performer may be included in "similar or the same characteristics (e.g., tastes)".

A characteristic (e.g., a taste) of the user 380 is estimated form data concerning the user 380 detected by the sensing device 310. For example, a plurality of classifications concerning the characteristic (e.g., the taste) are provided. The classifications may be hierarchical. The plurality of classifications include fields such as music, a hobby, and sports. For example, the field of sports includes sub-fields such as golf, baseball, and football. One sub-field may be divided into a plurality of groups (e.g., a specific baseball team and a specific player). Information such as words and images related to the characteristic is set in the fields, the sub-fields, the groups, and the like. The characteristic (e.g., the taste) of the user 380 is decided (estimated) from the set information and the data concerning the user 380. One user 380 may correspond to a plurality of characteristics (e.g., tastes).

The user 380 having a taste similar to the taste (e.g., a group of a specific player in the sub-field of baseball in the field of sports) of the first user 381 is determined as the second user 382. For example, the taste of the first user 381 is represented as numerical values in a plurality of evaluation parameters. On the other hand, the taste of the second user 382 is represented as numerical values in a plurality of evaluation parameters. For example, in the respective plurality of evaluation parameters, differences between the numerical values of the first user 381 and the numerical values of the second user 382 (a plurality of values of differences) are calculated. The plurality of values of differences are processed (e.g., totaled). For example, when a total of the plurality of values of differences is small, the users 380 are determines as having the same characteristic (e.g., taste).

An example in which this embodiment is applied to a concert is explained below. In this example, acquisition of information concerning the user 380 by the sensing device 310 is performed at least in the concert.

Figure 3:
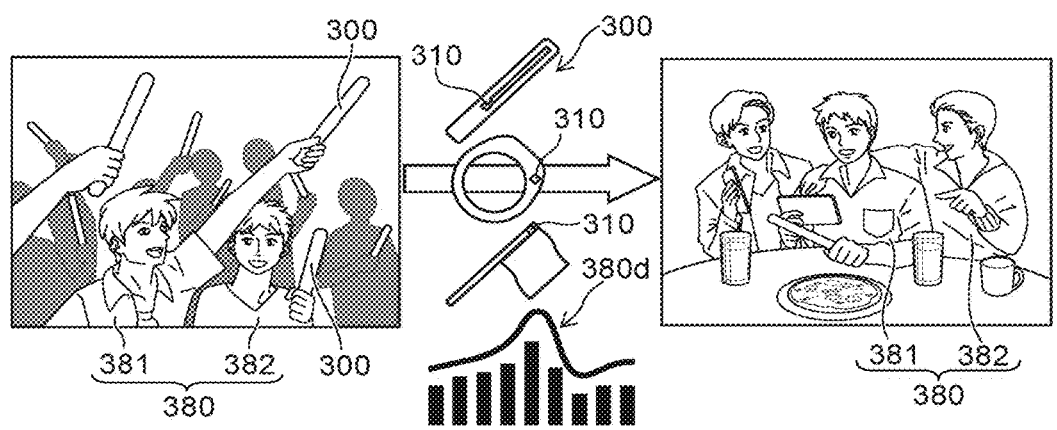
FIG. 3 is a schematic diagram illustrating the service providing system according to the first embodiment.

FIG. 3 is a schematic diagram illustrating the service providing system according to the first embodiment.

As shown in FIG. 3, for example, the plurality of users 380 (the first user 381, the second user 382, etc.) participate in an event (in this example, the concert). The users 380 use the goods 300 in the concert. The goods 300 are, for example, bar-like light emitting bodies, bracelets, or flags. The examples of the goods 300 are explained below. The sensing devices 310 are provided in the goods 300. For example, states of the bodies of the users 380 are detected by the sensing devices 310. Data 380*d* (information) concerning the detected states is provided to the cloud 350.

After the event ends, the plurality of users 380 (the first user 381, the second user 382, etc.) exchange information with one another. The plurality of users 380 may exchange information, for example, through a social network service. The plurality of users 380 may, for example, meet and exchange information with one another.

In the conventional social network service, deep emotion is expressed by a sentence, sound, an image, or the like.

In the first embodiment, deep emotion is represented by at least data detected by the sensing device 310. For example, the data detected by the sensing device 310 is event experience data. The data detected by the sensing device 310 is at least a part of the deep emotion experience UX (User Experience). In the embodiment, deep emotion can be expressed by the data detected by the sensing device 310 in addition to the expression of the deep emotion by the sentence, the sound, the image, or the like.

As explained above, in the first embodiment, for example, the deep emotion during the event is detected by the sensing device 310 provided in the goods 300. Deep emotion of the user 380 is converted into data. Concerning the deep emotion of the user 380 converted into the data, information exchange is performed among the plurality of users 380. The first embodiment provides a place of the information exchange concerning the deep emotion converted into the data.

Deep emotion of one user 380 spreads to the other users 380 better. Consequently, it is possible to realize dense communication. According to the first embodiment, it is possible to generate "core" data peculiar to a community.

An example of the first embodiment is further explained below.

FIG. 4A to FIG. 4D are schematic diagrams illustrating the service providing system according to the first embodiment.

Figure 4A:
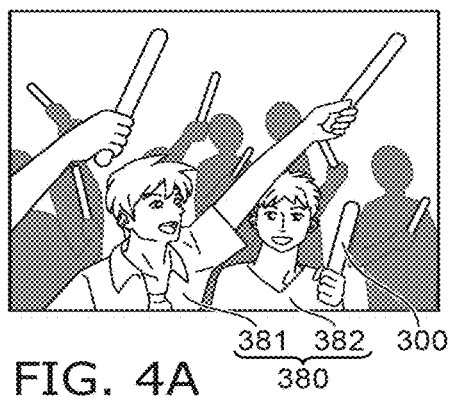
FIG. 4A to FIG. 4D are schematic diagrams illustrating the service providing system according to the first embodiment.

As shown in FIG. 4A, the user 380 participates in, for example, an event (e.g., a concert). In the event, the user 380 holds the goods 300. The sensing device 310 is provided in the goods 300. Data (an experience value) concerning the user 380 at the time when the user 380 participates in the event is measured by the sensing device 310. For example, the goods 300 emit light. The goods 300 of the respective plurality of users 380 are respectively operated by the plurality of users 380. Lights flashing according to movements of the respective plurality of users 380 are emitted from the goods 300. Thoughts of the respective plurality of users 380 are sent to the performer 385. The respective plurality of users 380 are connected to the performer 385 via the goods 300. The goods 300 are cheering goods. The goods 300 express sentiments of fans.

Figure 4B:
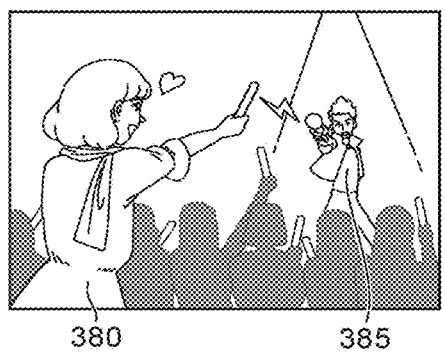

As shown in FIG. 4B, the performer 385 appears in the event. The performer 385 is, for example, an "idol". The user 380 participating in the event desires to touch the performer 385. For example, light emitted from the performer 385 is connected to the user 380. The light emitted from the performer 385 reaches the respective plurality of users 380.

Figure 4C:
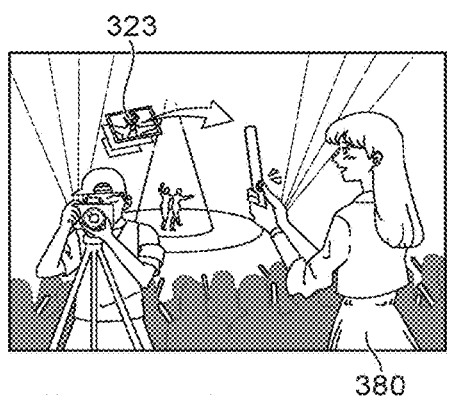

As shown in FIG. 4C, the user 380 participating in the event photographs a scene in which the user 380 feels deep emotion. A photographed image is supplied to, for example, the social network service. The image is applied to, for example, a commodity 323 (e.g., a poster). Since the scene in which the user 380 feels deep emotion is applied to the commodity 323 or the like, enjoyment of the user 380 increases.

Figure 4D:
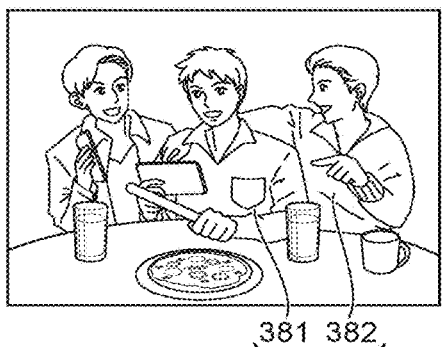

As shown in FIG. 4D, after the event, the plurality of users 380 exchange information. Fun memories in the event are recalled. The memories are shared by the plurality of users 380. A desire to spread deep emotion is realized among the plurality of users 380.

The first embodiment focuses on, for example, an essential desire of a person who experiences deep emotion. For example, when a person is moved, the person desires to speak to other people. When the person is moved, the person desires to record deep emotion. The person desires to record the entire deep emotion as much as possible. For example, the person desires to increases the deep emotion together with friends. According to the first embodiment, a degree of satisfaction of such an essential desire is improved.

Figure 5:
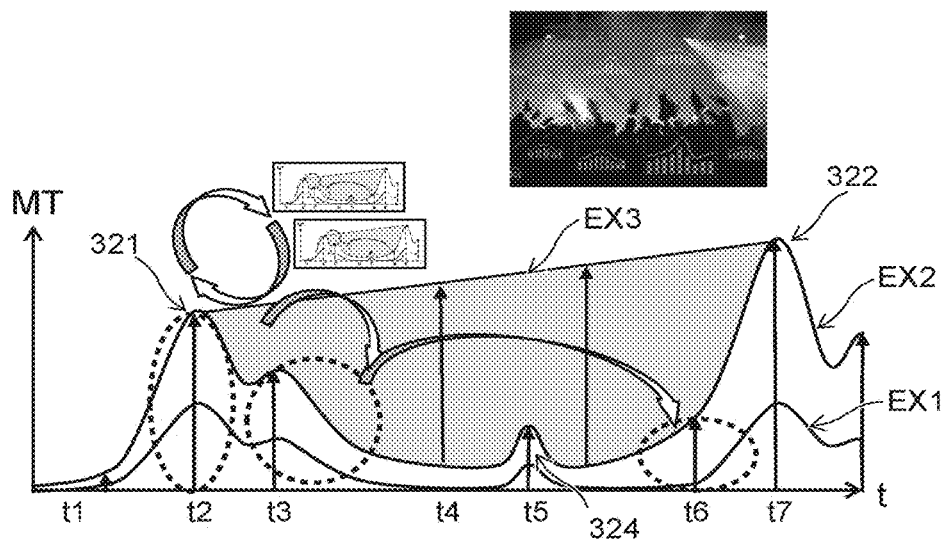
FIG. 5 is a schematic diagram illustrating the service providing system according to the first embodiment.

FIG. 5 is a schematic diagram illustrating the service providing system according to the first embodiment.

FIG. 5 shows an example of a change in motivation of a person. In this example, the user 380 participates in an event (e.g., a concert). The horizontal axis indicates time t. The vertical axis indicates motivation MT. The motivation MT includes a desire to purchase commodities related to the event. The commodities related to the event include, for example, hardware related to performers appearing in the event (e.g., a recording medium in which music, a video, and the like are recorded such as a poster) and software (e.g., information such as music and a video).

In FIG. 5, three examples (a first example EX1, a second example EX2, and a third example EX3) are shown concerning the change in the motivation MT. In the first example EX1, for example, the sensing device 310 is provided in goods used by the user 380 when the user 380 participates in the event.

In the second example EX2, the sensing device 310 is provided in the goods 330 used by the user 380 when the user 380 participates in the event. In the second example EX2, data based on a detection result of the sensing device 310 is exchanged. For example, a state and the like of the body of the user 380 during the event are detected by the sensing device 310. For example, a degree of cheering to the performer 385 is evaluated on the basis of a result of the detection. A result of the evaluation is transmitted to, for example, the goods 300. A difference between the user 380 and other participants may be displayed. In the second example EX2, for example, information exchange based on the data is performed between the user 380 and an organizer of the event. In the second example EX2, the information exchange based on the data may be performed among the plurality of users 380 participating in the event. The second example EX2 corresponds to examples in second to sixth embodiments explained below.

In the third example EX3, for example, the detection result by the sensing device 310 in the second example EX2 is further provided to the cloud 350. A community having a characteristic (e.g., a taste) similar to or the same as the characteristic (e.g., the taste) of the user 380 is formed on the basis of the detection result. In this case, for example, after the event ends, the plurality of users 380 perform information exchange with one another. The third example EX3 corresponds to an example in a seventh embodiment explained below.

First, the first example EX1 is explained. For example, the motivation MT is low at a first time t1 before the user 380 participates in a first event 321. The motivation MT is high at a second time t2 when the user 380 participates in the first event 321. After the first event 321 ends, the motivation MT decrease as time t elapses. Thereafter, at a third time t3, for example, the user 380 performs information exchange with other people. At the third time t3, the motivation MT increases again. Thereafter, the motivation MT decreases as time elapses. At a fourth time t4, the motivation MT is low. In this example, at a fifth time t5, the user 380 purchases a commodity 324 related to the first event 321. The commodity 324 is, for example, a recording medium in which video software is recorded. At the fifth time t5, the motivation MT increases. Thereafter, the motivation MT decreases as the time t elapses. Thereafter, the user 380 plans to participate in a second event 322. At a sixth time t6 before the second event 322, the motivation MT increases. At a seventh time t7 when the user 380 participates in the second event 2, the motivation MT is the maximum. After the end of the second event 322, the motivation MT decreases.

In the first example EX1, the motivation MT temporarily increases during the two events and during the purchase of the commodity 324. The motivation MT is not sufficiently high.

In the second example EX2, the motivation MT is higher than the motivation MT in the first example EX1 at the respective times. In the second example EX2, the user 380 uses the goods 300 provided with the sensing device 310. Consequently, the user 380 enjoys the event more. A degree of deep emotion is large in the user 380. Consequently, the motivation MT is improved. The user 380 enjoys the first event 321 more than in the case of the first example EX1. Further, since the user 380 enjoys the first event 321 more, the user 380 enjoys the second event 322 more. In the second example EX2, for example, the user 380 can increase deep emotion with the friends. Therefore, for example, the motivation MT in the second event 322 is higher than the motivation MT in the first event 321.

In the third example EX3, the plurality of users 380 included in one community performs information exchange using detection data detected by the sensing device 310. The information exchange is performed even after the event ends. Therefore, even after the event ends, for example, a desire to purchase the commodity 324 increases. Therefore, in the third example EX3, the motivation MT in a period between the first event 321 and the second event 322 can be set higher than the motivation MT in the second example EX2.

In the second example EX2, deep emotion can be further increased than in the first example EX1. Further, in the third example EX3, deep emotion in participation in one event continues to the next event. It is possible to further satisfy an essential desire of a person who experiences deep emotion. For example, deep emotion in an entertainment "E" is grasped in Things "T" (e.g., the sending device 310). The grasped deep emotion is amplified by the Internet "I" (the cloud 350). In the first embodiment, for example, EIoT (Entertainment Internet of Things) is provided.

Figure 6:
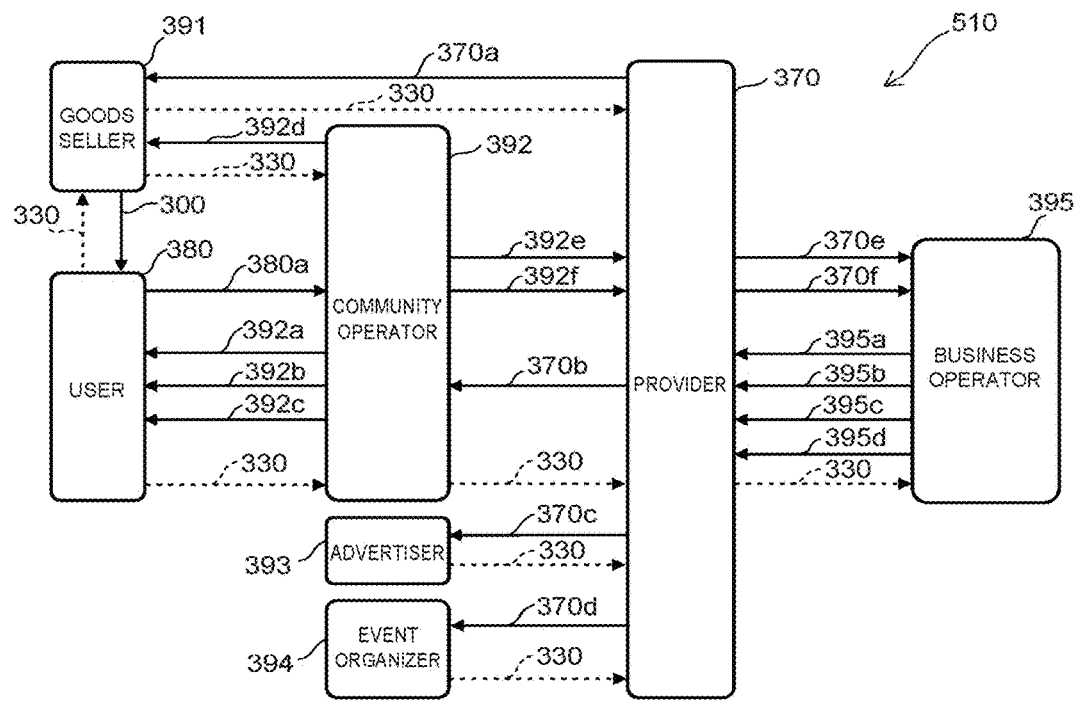
FIG. 6 is a schematic diagram illustrating the service providing system according to the first embodiment.

FIG. 6 is a schematic diagram illustrating the service providing system according to the first embodiment.

As shown in FIG. 6, in the service providing system 510, for example, information is provided to the user 380 by the provider 370. The provider 370 may be, for example, a "joint venture" type. The provision of a service to the user 380 may be performed directly or indirectly.

For example, the provider 370 provides authorization 370a to a goods seller 391. The goods seller 391 pays consideration 330 to the provider 370. In this embodiment, the consideration 330 is, for example, money. The consideration 330 may be a right (e.g., a right having an economical value).

The provider 370 may provide a service 370b to a community operator 392. The service 370b includes, for example, a "consultant" and a "solution". The community operator 392 pays the consideration 330 to the provider 370.

The community operator 392 provides official approval 392d to the goods seller 391. The goods seller 391 pays the consideration 330 to the community operator 392.

The goods seller 391 provides the goods 300 to the user 380. The user 380 pays the consideration 330 to the goods seller 391. The sensing device 310 (not shown in FIG. 6) is provided in the goods 300.

The user 380 participates in, for example, an event. For example, a state of the user 380 at the time when the user 380 participates in the event is detected by the sensing device 310. A result of the detection is provided to the community operator 392 as consumer data 380a (C data). The community operator 392 provides, for example, a social network service 392a to the user 380. The community operator 392 may provide, for example, "contents and an article" 392b to the user 380. The community operator 392 may provide, for example, an advertisement 392c to the user 380. The user 380 pays the consideration 330 to the community operator 392.

The community operator 392 provides business data 392e (B data) to the provider 370. The community operator 392 provides consumer data 392f (C data) to the provider 370. The consumer data 392f includes at least a part of the consumer data 380a.

The provider 370 may request an advertiser 393 to provide an advertisement 370c. The advertiser 393 pays the consideration 330 to the provider 370.

The provider 370 may provide a service 370d to the event organizer 394. The service 370d includes, for example, a "consultant" and a "solution". The event organizer 394 pays the consideration 330 to the provider 370.

The provider 370 may provide business data 370e (B data) to a business operator 395. The provider 370 may provide consumer data 370f (C data) to the business operator 395. The consumer data 370f includes at least a part of the consumer data 392f. The business operator 395 may provide a service of at least one of synthesis data 395a, image analysis 395b, data analysis 395c, and sound synthesis 395d to, for example, the provider 370. The business operator 395 may support the provider 370. The provider 370 pays the consideration 330 to the business operator 395.

Second Embodiment

A second embodiment relates to, for example, a service providing method and a service providing system performed on the basis of deep emotion experience UX. In the service providing method and the service providing system explained below, a participant corresponds to the user 380.

According to the second embodiment, the service providing system includes an acquiring unit and a providing unit. The acquiring unit acquires first action information concerning an action relating to an event of a first participant participating in the event. The providing unit provides a first service based on the first action information to the first participant.

Figure 7:
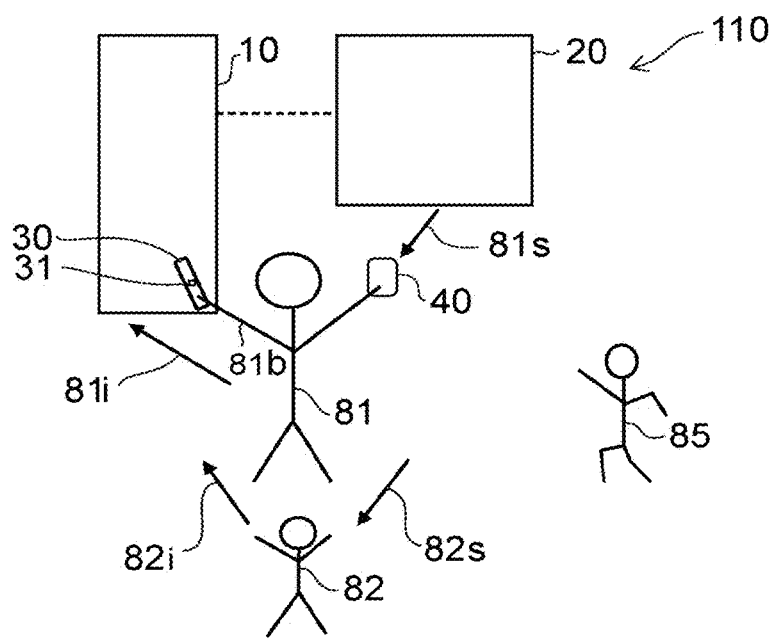
FIG. 7 is a schematic diagram illustrating the service providing system according to the second embodiment.

FIG. 7 is a schematic diagram illustrating the service providing system according to the second embodiment.

Figure 8:
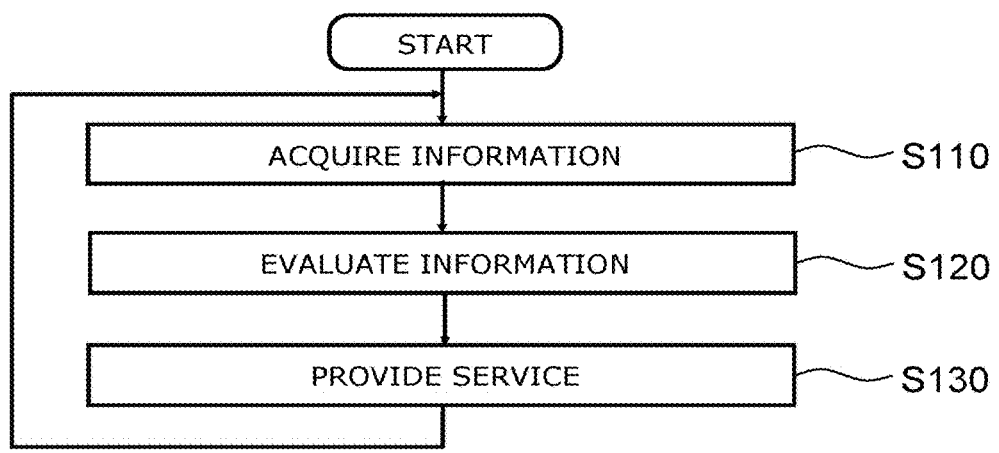
FIG. 8 is a flowchart illustrating the operation of the service providing system according to the second embodiment.

FIG. 8 is a flowchart illustrating the operation of the service providing system according to the second embodiment.

As shown in FIG. 7, a service providing system 110 according to this embodiment includes an acquiring unit 10 and a providing unit 20.

As shown in FIG. 8, the acquiring unit 10 acquires first action information 81i of a first participant 81 participating in an event (step S110).

The first participant 81 performs an action relating to the event. The first action information 81i is information concerning the action of the first participant 81 relating to the event.

The event includes, for example, a concert, a competition, a festival, an exhibition, and a sale. The competition relates to sports. The competition may include, for example, games (a card game, a board game, and an electronic game). The event may include, for example, a school festival, a wedding ceremony, travel, and a birthday party. A plurality of participants may participate in the event. Various examples of the event are explained below.

For example, a performer 85 is present in the event. The performer 85 includes, for example, at least any one of a singer, an actor, a dancer, an artist, an athlete, and an executer of a game. The performer 85 may include a producer or a creator relating to the event. The performer 85 includes, for example, a recorded video such as a movie, an artwork, food, and a product. The performer 85 includes another participant participating in the event.

In the following explanation, to simplify the explanation, it is assumed that the event is a concert of a singer.

The first participant 81 participates in the concert. The first participant 81 is a viewer. When the first participant 81 participates in the concert, the first participant 81 takes an action for cheering the performer 85 (e.g., a singer). For example, the first participant 81 performs a hand-clap, emits voice, swings the body, and dances according to a state of the performer 85. In the case of this example, the state of the performer 85 includes a state of at least any one of a song, music, and a dance of the performer 85. The state of the performer 85 may include at least any state of illumination, gas emission, and vibration.

For example, the first participant 81 sometimes holds a held object 30 such as a penlight that emits light. The first participant 81 sometimes moves the held object 30 according to the song and the dance of the performer 85. Such an action of the first participant 81 is included in the first action information 81i.

In the acquiring unit 10, an electronic device capable of acquiring the first action information 81i is used. The first participant 81 may be imaged and the acquiring unit 10 may acquire data of the imaging. As explained below, the first participant 81 may hold the held object 30 including a sensor (a first sensor 31). The first action information 81i of the first participant 81 may be obtained by the sensor. Various examples of the acquiring unit 10 are explained below.

The providing unit 20 provides a first service 81s based on the first action information 81i to the first participant 81.

For example, the first action 81i is evaluated (step S120 shown in FIG. 8). The evaluation may be performed in, for example, at least either one of the acquiring unit 10 and the providing unit 20. The evaluation may be performed in an electronic device different from the acquiring unit 10 and the providing unit 20.

For example, a degree of matching of a movement of the penlight of the first participant 81 with a state (a movement, rhythm of music, etc.) of the performer 85 is evaluated. For example, when a result of the evaluation reaches a standard, the first service 81s is provided to the first participant 81. The first service 81s may include, for example, a password for permitting viewing of a video. Various examples of the evaluation and various examples of the first service 81s are explained below.

As explained above, in the service providing system 110 according to this embodiment, the first service 81s based on the first action information 81i of the first participant 81 is provided to the first participant 81 (step S130 shown in FIG. 8).

Consequently, a service matching the first participant 81 is provided to the first participant 81. The system explained above is provided to the plurality of participants. Consequently, services more matching the respective plurality of participants are provided to the participants.

In the embodiment, the service is provided to the plurality of participants. For example, the acquiring unit 10 further acquires second action information 82i concerning an action relating to the event of a second participant 82 participating in the event. The providing unit 20 provides a second service 82s based on the second action information 82i to the second participant 82. When the second action information 82i is different from the first action information 81i, the second service 82s is different from the first service 81s. In this way, in the embodiment, a service provided on the basis of an action of a participant is different according to the action of the participant. When a threshold is provided concerning the action of the participant, even if the action of the participant is different, the same service is sometimes provided.

Several examples of the operation of the service providing system 110 according to this embodiment are explained below.

For example, the first participant 81 participating in the event performs a motion (a first action) for cheering the performer 85 is a venue of the event. For example, the first participant 81 moves a pen-type light according to a song and performance of the performer 85. For example, an acceleration sensor is provided in the pen-type light. A first action is detected by the acceleration sensor. The first action information 81i concerning the motion (the first action) of the first participant 81 is collated with, for example, information concerning a movement (e.g., a dance) of the performer 85. The information concerning the movement of the performer 85 is, for example, acquired in advance. The information concerning the movement of the performer 85 may be obtained from imaging data of the performer 85 in the venue of the event. For example, an image analyzing device is used.

The collation of the first action information 81i of the first participant 81 and, for example, the information concerning the movement of the performer 85 is performed by, for example, an information processing device (e.g., a computer).

For example, the first action information 81i is represented as a chart. For example, a portion of the chart of the first action information 81i matching a chart of the movement of the performer 85 is extracted. According to the matching portion, viewing permission for prepared information (e.g., video information) is provided to the first participant 81. According to the matching portion, viewing is permitted to the first participant 81 relating to the prepared information (e.g., the video information).

For example, the first participant 81 has an electronic information terminal device 40. The information terminal device 40 may be, for example, a portable type. A recognition number (an ID number) corresponding to the first participant 81 is given to the information terminal device 40. For example, a password for the viewing permission for the prepared information is transmitted to the information terminal device 40.

The providing unit 20 provides the first service 81s to the first participant 81 on the basis of a degree of cheering to the performer 85 performed by the first participant 81. For example, content of the first service 81s is changed according to the degree of the cheering to the performer 85 performed by the first participant 81. For example, content of the first service 81s at the time when the degree of the cheering is high is set to more please the participants than content of the first service 81s at the time when the degree of the cheering is low. Therefore, the first participant 81 tries to perform better cheering such that the first participant 81 can obtain a better first service 81s. Therefore, the event is more preferentially cheered by participants such as the first participant 81. Since the performer 85 is cheered better, the performance of the event is improved. A degree of satisfaction of the first participant 81 increases. A value of the event further increases.

As explained above, according to this embodiment, the service matching the first participant 81 can be provided to the first participant 81. In addition, the performance of the event is improved. The value of the event increases. As a result, a degree of satisfaction of the participants increases.

For example, when the event is a competition of sports, the first participant 81 watches the competition. The performer 85 is an athlete participating in the competition. The first participant 81 cheers a team or the athlete. The first participant 81 holds the held object 30 such as a flag or a megaphone. The first sensor 31 is provided in the held object 30. The first sensor 31 includes an acceleration sensor and a microphone. The first action information 81i (a motion, voice, etc.) of the first participant 81 in a venue of the event is detected by the first sensor 31. The first action information 81i is converted into, for example, information in which set evaluation parameters are used. The converted first action information 81i is collated with parameters of the movement of the athlete. For example, content of the first service 81s is changed according to a degree of matching of the parameters. Consequently, it is possible to provide a service matching the first participant 81 to the first participant 81. Further, the performance of the event is improved and the value of the event is increased by the cheering of the participants such as the first participant 81.

As explained above, in the embodiment, the first action information 81i is, for example, information concerning the first participant 81 at the time when the first participant 81 participates in the event. For example, the first action information 81i relates to at least any one of a movement of a first body 81b of the first participant 81, a state of the first body 81b, and voice of the first participant 81. The movement of the first body 81b includes, for example, a movement of at least any one of a hand, a foot, the trunk, and the head of the first participant 81. The movement of the first body 81b includes, for example, at least either one of a hand-clap and a dance of the first participant 81. An example of the state of the first body 81b is explained below. The voice of the first participant 81 includes a song of the first participant 81.

The first action information 81i may be acquired by, for example, the first sensor 31. That is, the acquiring unit 10 may include the first sensor 31. The first sensor 31 is held by the first participant 81. The first sensor 31 acquires information concerning the first action information 81i.

As shown in FIG. 7, for example, first sensor 31 is fixed to the held object 30. In the embodiment, the first sensor 31 may be attached to the held object 30. The held object 30 is held by the first participant 81. The held object 30 is attached to the first body 81b of the first participant 81.

Figure 9A:
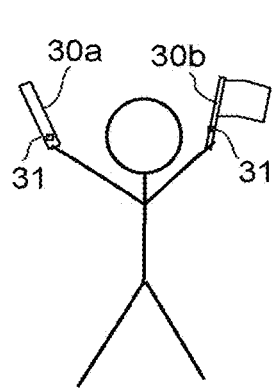
FIG. 9A to FIG. 9C are schematic diagrams illustrating the service providing system according to the second embodiment.
Figure 9B:
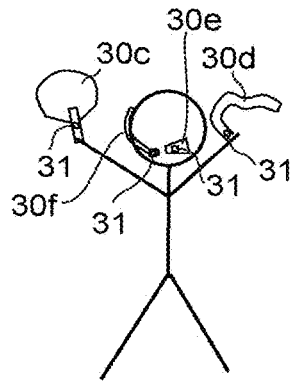
Figure 9C:
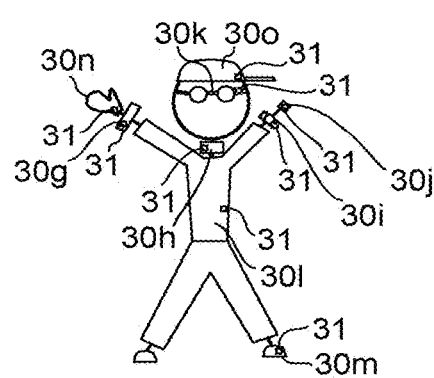

FIG. 9A to FIG. 9C are schematic diagrams illustrating the service providing system according to the second embodiment.

As shown in FIG. 9A, the held object 30 includes a light emitting device 30a (e.g., a light). The light emitting device 30a has, for example, a bar shape. The light emitting device 30a is, for example, a pen-type light. The held object 30 may include a flag-like body 30b.

As shown in FIG. 9B, the held object 30 may include a fan-like body 30c. The held-object 30 may include a cloth-like body 30d. The held object 30 may include a megaphone 30e. The megaphone 30e controls, for example, a direction of sound. The megaphone 30e may electronically increase the loudness of sound (voice). The held object 30 may include a microphone 30f.

As shown in FIG. 9C, the held object 30 may include a bracelet 30g. The held object 30 may include a necklace 30h. The held object 30 may include a watch 30i. The held object 30 may include a finger ring 30j. The held object 30 may include eyeglasses 30k. The held object 30 may include clothes 30l. The held object 30 may include a shoe 30m. The held object 30 may include a glove 30n. The held object 30 may include a cap 30o. The held object 30 may include the information terminal device 40 (see FIG. 7). The held object 30 may include a headband, a balloon, a mascot, a seat cushion, a ticket holder, a tag, an earring, a name card, a badge, a sticker, an accessory (e.g., including at least either one of a headband and an Aliceband), a headphone, an earphone, and a hearing aid.

The first sensor 31 is provided in the held object 30. The first sensor 31 includes, for example, an acceleration sensor. The first sensor 31 detects the first action information 81i including a movement of the first body 81b of the first participant 81. The first sensor 31 detects at least any one of acceleration, speed, and a moving direction of at least a part of the first body 81b of the first participant 81. That is, the first service 81s is changed on the basis of at least any one of the acceleration, the speed, and the moving speed of at least a part of the first body 81b.

When the first sensor 31 includes a microphone, the first sensor 31 detects the first action information 81i including voice of the first participant 81.

Figure 10:
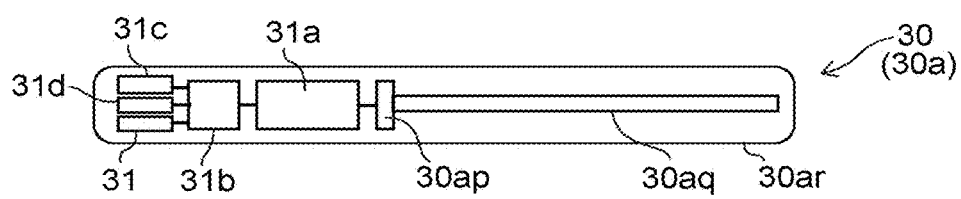
FIG. 10 is a schematic diagram illustrating the service providing system according to the second embodiment.

FIG. 10 is a schematic diagram illustrating the service providing system according to the second embodiment.

FIG. 10 illustrates the light emitting device 30a used as the held object 30.

As shown in FIG. 10, the light emitting device 30a includes, for example, a light emitting unit 30ap. In the light emitting unit 30ap, for example, an LED is used. The light emitting unit 30ap may be an organic light emitting body. The light emitting device 30a may include a light guide body 30aq.

The light emitting device 30a may include, for example, a battery 31a. The first sensor 31 is provided in a housing 30ar of the light emitting device 30a. A first processing device 31b, a first communication unit 31c, and a first memory 31d (a storing unit) may be provided in the housing 30ar. As the first processing device 31b, for example, a semiconductor device such as a CPU is used. The first processing device 31b processes a signal of a detection result of the first sensor 31. The first communication unit 31c transmits the signal concerning the detection result to the outside. The first communication unit 31c may receive a signal from the outside. Information concerning the detection result is stored in the first memory 31d. The first memory 31d stores information concerning the operation of the first processing device 31b. The first memory 31d may store information concerning the first service 81s.

In the embodiment, for example, the first service 81s may be changed on the basis of an operation state of the light emitting device 30a. The operation of the light emission of the light emitting device 30a is switched by the first participant 81 according to, for example, performance of a song, a dance, or the like of the performer 85. When appropriate switching is performed, a high-level first service 81s may be provided.

The first action information 81i of the first participant 81 may be acquired by other methods.

Figure 11:
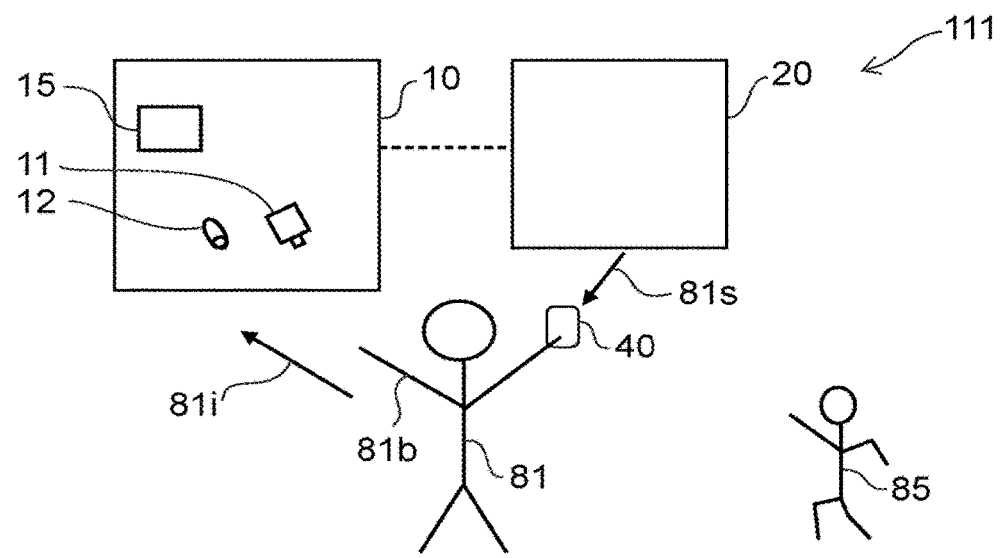
FIG. 11 is a schematic diagram illustrating another service providing system according to the second embodiment.

FIG. 11 is a schematic diagram illustrating another service providing system according to the second embodiment.

As shown in FIG. 11, in another service providing system 111 according to the embodiment, the acquiring unit 10 includes at least either one of an imaging unit 11 and a microphone 12. The imaging unit 11 acquires image data of the first participant 81. The image data is image data including the first participant 81 at the time when the first participant 81 is present in a venue of an event. The microphone 12 acquires voice data of the first participant 81. The sound data is voice data including voice of the first participant 81 at the time when the first participant 81 participates in the event. The imaging unit 11 and the microphone 12 are provided in, for example, the venue of the event. The number of imaging units 11 may be plural. The number of imaging units 11 may be decided according to the breadth of the venue. The image data includes at least either one of a still image and a moving image.

Further, the acquiring unit 10 may acquire data acquired by a camera or a microphone not included in the acquiring unit 10. In this case, an obtaining unit 15 is provided in the acquiring unit 10. The obtaining unit 15 obtains, for example, at least either one of separately acquired image data of the first participant 81 and separately acquired voice data of the first participant 81.

As explained above, in the embodiment, the first action information 81i of the first participant 81 in the acquiring unit 10 is acquired by various methods.

In the embodiment, the first service 81s is provided on the basis of detection results of a motion and voice of the first participant 81 by the first sensor 31 provided in the held object 30 held by the first participant 81 participating in the event. The first service 81s is changed according to the detection results. The held object 30 includes, for example, cheering goods used for cheering of an event.

The first action information 81i may include a state of the first body 81b of the first participant 81. The state of the first body 81b includes, for example, at least either one of a heart rate and a blood pressure of the first body 81b. Information concerning the heart rate and the blood pressure is obtained by sensors or the like provided in various held objects 30 or the like held by the first participant 81. The information concerning the heart rate and the blood pressure may be obtained by a sensor or the like provided in the information terminal device 40.

For example, at least either one of the heart rate and the blood pressure changes according to a degree of cheering of the event by the first participant 81. For example, at least either one of the heart rate and the blood pressure changes according to a state in which the first participant 81 enjoys the event. The providing unit 20 provides the first service 81s on the basis of the information including at least either one of the heart rate and the blood pressure of the first participant 81. It is possible to provide a service matching the first participant 81 to the first participant 81.

The first action information 81i may include information input to an electronic device by the first participant 81. The information is performed by, for example, the obtaining unit 15 included in the acquiring unit 10. For example, as the electronic device, the held object 30 or the information terminal device 40 may be used. The first action information 81i may include, for example, information input by the first participant 81 when the first participant 81 participates in the event.

Further, the first action information 81i may include, for example, information input by the first participant 81 before or after the first participant 81 participates in the event. For example, a period for applying for participation in the event is provided before a specific period of the event. In the period, the first participant 81 sometimes takes an action for cheering the event. For example, after the specific period of the event, a participant sometimes expresses an impression or an evaluation result concerning the event. Such expression after the event is included in the action of the first participant 81 for cheering the event. The action for cheering the event includes an action for pointing out improvement points of the event.

The first service 81s is provided on the basis of the first action information including the information input to the electronic device before or after the first participant 81 participates in the event. Therefore, a range of actions for cheering the event expands. It is possible to provide a service more matching the first participant 81.

In this embodiment, the first action information 81i includes information concerning an action (including a remark) of the first participant 81 in the venue of the event. For example, the first action information 81i includes information concerning a motion for cheering the performer 85 of the event. The cheering motion is, for example, a conscious motion. The first action information 81i includes the information concerning a motion corresponding to the performer 85. The motion corresponding to the performer 85 is, for example, a conscious motion corresponding to a movement of the performer 85. The first action information 81i may include an unconscious reaction of the first participant 81 in the event. The first action information 81i may include an action for observing manners of the first participant 81 in the event. The manners include, for example, a state and the like of the first participant 81 in an exit from the venue after the end of the event and in going back home.

An example of evaluation of the first action information 81i is explained below.

Figure 12:
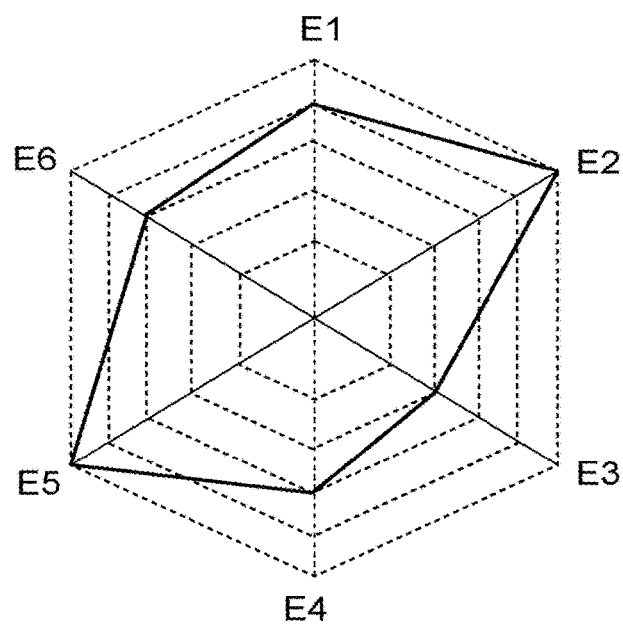
FIG. 12 is a schematic diagram illustrating the service providing system according to the second embodiment.

FIG. 12 is a schematic diagram illustrating the service providing system according to the second embodiment.

FIG. 12 illustrates evaluation of the first action information 81i.

The first action information 81i is evaluated, for example, on the basis of evaluation items. For example, a motion of the first body 81b of the first participant 81 detected by the first sensor 31 is evaluated. A result of the evaluation is indicated by, for example, a radar chart. The evaluation result may be indicated by, for example, at least any one of a graph, a sign, an illustration, a pattern, and an avatar (a doll). The evaluation result may be represented by, for example, at least either one of gas and liquid. The evaluation result may be indicated by a change in a configuration of a displayed image (e.g., a change in a frame layout of a cartoon). As visualized representation of the evaluation result, various representations may be applied for each of events.

The evaluation items include, for example, a synchronization degree E1 with the performer 85. The synchronization degree E1 includes a coincidence degree of timings of an action of the first participant 81 and a movement of the performer 85.

The evaluation items include a synchronization degree E2 with another participant (e.g., the second participant 82). The synchronization degree E2 includes a coincidence degree of timings of a movement of the first participant 81 and a movement of another participant (the second participant 82) different from the first participant 81.

The evaluation items include, for example, a movement completion degree E3. The movement completion degree E3 includes a coincidence degree of a movement (e.g., a dance) of the first participant 81 and a movement decided in advance. The movement completion degree E3 may include the magnitude and time of a movement. The magnitude of the movement is the size of a range in which the first body 81b of the first participant 81 moves. The time of the movement is the length of time in which the first body 81b of the first participant 81 is exercised.

For example, data obtained by at least any one of the first sensor 31, the imaging unit 11, and the microphone 12 is evaluated on the basis of the evaluation items of the synchronization degree E1 with the performer 85, the synchronization degree E2 with the other participant, and the movement completion degree E3.

The evaluation degrees may include, for example, an enthusiasm degree E4. The enthusiasm degree E4 may include, for example, a concentration degree of the first participant 81. For example, data including at least either one of a heart rate and a blood pressure of the first body 81b is evaluated as the evaluation item of the enthusiasm degree E4.

The evaluation items may include, for example, a contribution degree E5. The contribution degree E5 includes evaluation of an action (a remark) for carrying out the event better. For example, the action (including the remark) may include, for example, a spontaneous action of the first participant 81. For example, the contribution degree E5 may include an action (including a remark) for praising the event. The contribution degree E5 may include an action (including a remark) for proposing improvement points concerning the event. The contribution degree E5 may include an action (a remark) for solving a trouble in the event. For example, information concerning an action (including a remark) of the first participant 81 in the venue of the event is acquired by the first sensor 31, the imaging unit 11, the microphone 12, and the obtaining unit 15. The acquisition of the information by the obtaining unit 15 includes acquisition from an electronic information network such as a Web. Such information is evaluated as data of the contribution degree E5.

The evaluation items may include, for example, a cooperation degree E6. The cooperation degree E6 includes, for example, an observance degree to an instruction related to operation of the event. For example, the instruction concerning the operation includes an instruction for movement in the event venue (including an instruction for entrance and exit, an instruction for a rest, and a seat instruction). The instruction concerning the operation may include, for example, instructions performed before the event is held and after the event is held.

For example, in one example of the embodiment, the obtained first action information 81i is evaluated on the basis of evaluation items (e.g., the evaluation items explained with reference to FIG. 12) (step S120). The first service 81s is changed on the basis of a result of the evaluation. The evaluation items include, for example, a first relation degree. The first relation degree includes a correlation between provided information including at least either one of music and a video provided in the event and the first action information 81i. The first relation degree includes, for example, the synchronization degree E1 with the performer 85.

The evaluation items may include, for example, a second relation degree. The second relation degree includes a correlation between second action information concerning a second action relating to an action relating to the event of the second participant 82 participating in the event and the first action information 81i. The second relation degree includes the synchronization degree E2 with the second participant 82.

As explained above, in the embodiment, various modifications of the evaluation items are possible.

The processing according to the embodiment may be carried out by at least either one of the acquiring unit 10 and the providing unit 20.

In the embodiment, processing explained below may be carried out.

For example, information concerning the strength of a motion of the first participant 81 is acquired by an acceleration sensor. The information corresponds to an excitement degree of the first participant 81. At least either one of an average per time of the excitement degree of the first participant 81 and a difference between the excitement degree of the first participant 81 and an average of excitement degrees of the other participants of the event is evaluated.

For example, a difference between a sense of rhythm of the first participant 81 and at least either one of a tempo and rhythm of music is evaluated by the acceleration sensor.

For example, the number of acquisitions of communication is evaluated from information concerning a reception history of visible light communication.

For example, at least either one of differences between an evaluation result of the first participant 81 and an average of the other participants and a high-ranked participant in evaluation results among the other participants is evaluated from information concerning communication with a peripheral device. A harmony degree of the first participant 81 with participants around the first participant 81 is evaluated from the information concerning the communication with the peripheral device.

At least either one of the number and a distribution degree of bookmarks of parts that the first participant 81 considers nice is evaluated on the basis of information concerning a button pressing motion of the first participant 81 and a detection result in the acceleration sensor.

In a technique for the measurement and the determination, for example, at least any one of an acceleration sensor, a microphone, a heartbeat and image recognition technique, and the like is used.

A target to be measured and determined includes, for example, at least any one of a venue music, an idol, spectators, and the like.

In one example, acceleration sensor data is collected in an arithmetic device in a venue by wireless communication from a device held by a performer and devices held by spectators. Movement data (acceleration sensor data) of the performer and movement data of the spectators are compared. It is determined that movements of high-ranked one hundred spectators who transmit the movement data close to the movement data of the performer match the movement of the spectator.

In another example, data concerning at least any one of movement amounts, accelerations, and times in upward and downward, left and right, and front and rear directions, is measured by an acceleration sensor incorporated in a penlight swung by the spectator participating in a concert. The measured data is saved in a memory incorporated in the penlight. A movement of the performer is measured simultaneously with the processing explained above. The measurement is performed by, for example, an acceleration sensor incorporated in a terminal such as a microphone or an accessory held by the performer. The measurement is performed by an external image analyzing device. The data is collected in the arithmetic device in the venue by wireless communication and uploaded to a server on a cloud. The spectator is capable of confirming a measurement result from the memory via a portable terminal or a personal computer owned by the individual, comparing the measurement result and a measurement result of the performer present on the server, and downloading moving image data, sound data, an advertisement, or a benefit set in advance stepwise according to the number of matching parts.

In still another example, when the spectator suddenly swings the penlight, the device mounted with the acceleration sensor and the memory measures and records time when the penlights are swung and duration of the swing. The spectator can collates information corresponding to the time with information having a time line accumulated in the server by an event operator. For example, the information is content of stage effects at the time, content of microphone performance of the performer recorded at the time, or a standing position, a body motion, or the like of the performer measured by the external image analyzing device at the time. Contents linked to these kinds of information are present. The spectator can confirm the contents with the portable terminal or the personal computer.

In still another example, choreography of a cheering motion using a penlight-type device is uploaded to the server by a first spectator together with an explanation of the cheering motion and a measurement result of an acceleration sensor provided in the penlight-type device in advance before the start of the event. A second spectator holds the penlight-type device and imitates a movement of the first spectator before the start of the event or during the event and uploads a measurement result of the acceleration sensor recorded in the same manner and setting of colors to the server. The server measures the number of matches of the measurement results of the first spectator and the second spectator and presents an evaluation result to the first and second spectators stepwise. A download right of contents is sent from the first spectator or the operator side according to the evaluation result.

In still another example, when light from a visible light communication transmitting unit held by an idol is irradiated on a visible light communication receiving unit incorporated in a fan-shaped device or the like held by the spectator, the device records at least either one of the number of times of light reception and a pulse signal. During server connection, the spectator can obtain an acquisition right of contents set by the operator side according to at least either one of the number of times of light reception and the pulse signal. At least either one of infrared communication and acoustic wave communication may be used.

In still another example, when the operator instructs, by voice, the spectators to wait in seats, determination is performed according to whether a signal of a wireless communication device with reduced radio wave intensity can be received in terminals held by the spectators waiting in the seats. When movement is urged by a voice instruction, a code for proving a download right of contents is transmitted by the same wireless communication device. Only the spectators observing the instruction can receive the code. Alternatively, different data is transmitted from a short-range wireless communication terminal set in an exit according to timing of the movement instruction and integrated with seat information saved in the terminals of the spectators. Then, the download right of the contents can be realized.

An example of the first service 81s supplied from the providing unit 20 to the first participant 81 is explained.

The first service 81s may include, for example, display of the first action information 81i acquired by the acquiring unit 10. For example, when the first action information 81i includes a motion for cheering the performer 85, display of a time when the cheering motion is carried out may be provided as the first service 81s. The display may be performed using a figure or the like that can be easily visually recognized.

The first service 81s may include, for example, display of an evaluation result of the first action information 81i. For example, when the first action information 81i includes the motion for cheering the performer 85, display of an evaluation result of the cheering motion may be provided as the first service 81s. For example, the chart illustrated in FIG. 12 may be provided. The display in this case may also be performed using the figure or the like that can be easily visually recognized.

The figure may have a geometrical pattern such as a polygon. The figure may have a shape representing a person. The figure may have a shape of an object held by the person or a shape of clothes or the like (including a helmet) worn by the person. For example, the object, the clothes, or the like may be changed according to the evaluation result based on the first action information 81i.

The first service 81s may include, for example, information concerning at least any one of a video, an image (e.g., an illustration and a photograph), music, and sound. These kinds of information may be, for example, information concerning an event. These kinds of information may be, for example, information concerning the performer 85. These kinds of information may be information concerning an event different from the event in which the first participant 81 participates. These kinds of information may be information concerning a performer different from the performer 85 of the event in which the first participant 81 participates. These kinds of information may be provided as the first service 81s. The first service 81s may be a password that enables browsing of the information.

The first service 81s may include, for example, information concerning an organizer, information concerning a cooperator, information concerning details of organizing, and information concerning a history of the event in which the first participant 81 participates and information concerning other events related to the event.

The first service 81s may include, for example, information concerning a venue of the event in which the first participant 81 participates, information concerning an area around the venue (transportation means, parking lots, restaurants, and the like), information concerning news relating to the periphery of the venue, and information concerning weather of a date when the event is held.

The first service 81s may include, for example, information concerning the other participants participating in the event. The first service 81s may include an advertisement. The first service 81s may include information concerning other events, foods and drinks, recipes, travel, education, beauty treatment, and health.

The first service 81s may include a tangible object other than the information. The tangible object includes, for example, at least any one of a storage medium including a video and music, a photograph, and goods.

The first service 81s may include, for example, at least any one of a gift commodity, a gift certificate, a financial product, and reservation of a commodity.

The first service 81s may be, for example, transferrable from the first participant 81 to others. For example, the first service 81s and the information concerning the first service 81s may be assignable from the first participant 81 to the other participants of the event. For example, the first service 81s (including, for example, at least any one of an image, sound, and a password) obtained by the first participant 81 may be assignable to another participant. For example, the assignment may be based communication to the operator of the event and approval of the event by the operator.

In one example of the embodiment, the obtained first action information 81i is evaluated on the basis of the evaluation items (step S120). The first service 81s is changed on the basis of a result of the evaluation. The first service 81s may include at least any one of first image information created on the basis of the first action information 81i, second image information created on the basis of the result of the evaluation, third image information concerning the event, video information concerning the event, music information concerning the event, and sound information concerning the event.

As explained above, the various modifications of the first service 81s are possible.

An example of a method of providing the first service 81s is explained.

The first service 81s may be provided to, for example, the first participant 81 in the venue of the event. The first service 81s may be provided in, for example, a goods shop annexed to the event venue.

The first service 81s may be provided via, for example, an electronic Web. The Web may include an SNS (Social Network Service) provided concerning the event. The Web may include an electronic bulletin board. The first service 81s may be provided by a mail order by the electronic Web. The provision by the Web is performed by, for example, an organization operating the event (an operation company, a company entrusted with the operation, etc.).

The first service 81s may be provided by, for example, a digital signage. The first service 81s may be provided by, for example, a vending machine.

The first service 81s may be provided via the held object 30 held by the first participant 81. As explained above, when the first participant 81 holds the held object 30 (a pen-type light) for cheering, information may be transmitted to the held object 30 as the first service 81s. For example, the information may include a password for enabling viewing of specific information.

For example, the held object 30 may be designed uniquely for the event. For example, information concerning the performer 85 of the event is stored in the first memory 31d provided in the held object 30. The held object 30 may be sold in a state in which the specific information is stored in the first memory 31d. Alternatively, the first participant 81 may store, for example, the specific information downloaded via the Web in the first memory 31d of the held object 30. The first service 81s may be a password relating to the specific information. The provision of the password may be performed via the first communication unit 31c of the held object 30. The provision of the password may be performed, for example, via the information terminal device 40 owned by the first participant 81.

The first service 81s may include a password for download of software such as application software or data to be distributed. The first service 81s may include driver software for using various electronic data provided as the first service 81s.

Further, access to various kinds of information may be enabled on the basis of the evaluation result of the first action information 81i. That is, for example, the first participant 81 may be recognized in the server. The first participant 81 may be enabled to access predetermined information without inputting a password.

In the embodiment, the provision of the first service 81s to the first participant 81 includes, for example, enabling access by the first participant 81 to data (including software) provided to the first participant 81 concerning the event.

In this way, the various modifications of the method of providing the first service 81s are possible.

In this embodiment, for example, acceleration sensors are provided in goods (the held object 30, etc.) for cheering the performer 85 in the event. A movement (a motion of cheering) of the first participant 81 is detected by the acceleration sensor. A result the detection (an action history of the first participant 81) is visualized and displayed. The first participant 81 can enjoy the event more by viewing this display. The first participant 81 can compete with the other participants. Contents (a photograph, a video, etc.) distributed according to an action history are changed according to a participant. An advertisement or a commodity displayed according to the action history is changed by the participant.

In this embodiment, for example, information concerning the contents (the photograph, the video, etc.) is stored in the goods for cheering the performer 85. Access to the contents may be unlocked according to the detected first action information 81i.

As explained above, in this embodiment, actions and states of the user participating in the event are detected. A result of the detection is converted into parameters. On the other hand, contents are converted into parameters. The detection result converted into parameters and the contents converted into the parameters are collated. A service (contents) to be provided is changed according to a collation result. In this embodiment, for example, at least either one of actions and states of the participant participating in the event are detected by the first sensor 31. A result of the detection is evaluated according to the set evaluation items. For example, scoring is performed. A service associated with the score is provided to the participant on the basis of a result of the evaluation. The service includes at least either one of contents (information) and a tangible object.

In this embodiment, for example, the first participant 81 participating in the event carries out the motion (the first action) for cheering the performer 85. The first action information 81i concerning the first action is detected by the first sensor 31 (e.g., the acceleration sensor) provided in the held object 30 (e.g., the pen-type light) held by the first participant 81. The first action information 81i is processed by, for example, the first processing device 31b provided in the held object 30. The first action information 81i is evaluated on the basis of the evaluation items. The first action information 81i is, for example, converted into a numerical value. Contents including at least any one of a photograph, a video, and sound are provided as the first service 81s on the basis of the first action information 81i. Information concerning the contents may be stored in the held object 30 in advance. A service to be provided changes according to an action of each of the participants. In this example, it is possible to provide the service without communication.

In this embodiment, the service may be provided using communication. For example, the light emitting device 30a (e.g., the pen-type light) is used as the held object 30. Light emission of the held object 30 is controlled by, for example, the first processing device 31b. For the control, for example, a computer program stored in the first memory 31d provided in the held object 30 is used. The control may be associated with the other participants. Vibration of the light emitting device 30a may be controlled by the computer program. The control may be performed according to a signal (information) transmitted during the event. The first sensor 31 (the acceleration sensor, etc.) is provided in the held object 30. For example, after the event, the acquired first action information 81i is evaluated. An access authority to a service prepared on the cloud is changed on the basis of a result of the evaluation. In this example, the held object 30 is used as a device for cheering the performer 85 during the event. Further, the held object 30 is used as a device for transmitting the first action information 81i. Further, the held object 30 is used as a device capable of exchanging contents based on the cloud service.

According to the embodiment, it is possible to provide the service providing system that can provide a service more suitable for participants participating in an event to the participants.

In the embodiment, an event is held in a specific period. The event may include at least either one of an amusement park and a place for sightseeing. The event may be held in a fixed place. The event may be simultaneously held in a plurality of places.

In this embodiment, the first action information 81i may include at least either one of an action and an experience of the first participant 81 before participating in the event. The action and the experience of the first participant 81 before participating in the event may include, for example, creating a computer program concerning a relation between a motion and a way of flashing of a penlight and uploading the computer program. The action and the experience of the first participant 81 before participating in the event may include, for example, downloading a computer program concerning a relation between a motion and a way of flashing of a penlight. The action and the experience of the first participant 81 before participating in the event may include talking about a computer program concerning a relation between a motion and a way of flashing of a penlight. The action and the experience of the first participant 81 before participating in the event may include talking about how to participate in the event and how to involved in the event. The action and the experience of the first participant 81 before participating in the event may include talking about how to dispose of the event.

In the embodiment, the first action information 81i may include at least either one of an action and an experience of the first participant 81 after participating in the event.

Third Embodiment

In a third embodiment, the first action information 81*i* of the first participant 81 includes, for example, purchase information of the first participant 81 related to an event. For example, the first participant 81 purchases goods and the like relating to the event. The first action information 81*i* may include a history of such a purchase. The purchase history changes according to a degree of cheering of the event. The purchase history is obtained by a detection system such as a POS (Point of Sales System). A record of such a purchase is obtained from a communication record via the Internet.

The first action information 81*i* may include, for example, information concerning a communication record of the first participant 81. The first participant 81 has, for example, the information terminal device 40. The first action information 81*i* may include a communication record of communication via the information terminal device 40. The communication record may include a record of communication such as a comment of the first participant 81. The first action information 81*i* may include, for example, a search history of the first participant 81.

The communication record is obtained from, for example, a communication record of the information terminal device 40. The communication record is obtained from, for example, a communication record of communication via the Internet. The information terminal device 40 includes, for example, a telephone and a personal computer. A form of the information terminal device 40 is optional.

The first action information 81*i* may include, for example, position information of the first participant 81. The first participant 81 visits various places relating to the event. It is possible to estimate a degree of cheering of the event by the first participant 81 according to the position information of the first participant 81.

The first action information 81*i* may include information input from the first participant 81. For example, the first action information 81*i* may include a reply of the first participant 81 to a question.

Evaluation items relating to the first action information 81*i* may include, for example, participation rates of the first participant 81 in various events. The evaluation items may include, for example, an amount of money consumed by the first participant 81 concerning the event. The evaluation items may include, for example, a frequency of purchase by the first participant 81 relating to the event. The purchase relating to the event includes, for example, purchase of goods relating to the event.

The evaluation items of the first action information 81*i* may include a degree of development of the first participant 81 relating to the event. The evaluation items of the first action information 81*i* may include a degree of planning of the first participant 81 relating to the event. For example, the first participant 81 sometimes performs an action for supporting the event separately from a management organization of the event. For example, the first participant 81 sometimes sends a comment concerning the event via the Internet. The first participant 81 sometimes performs an appeal concerning the event. The first action information 81*i* may include information concerning such actions.

The first action information 81*i* may include information concerning a time of the first participant 81 consumed concerning the event. The first action information 81*i* may include information concerning the number of acquaintances in an SNS. The first action information 81*i* may include information concerning the number of times of invitation to events different from the event in which the first participant 81 participates. The first action information 81*i* may include information concerning at least either one of lateness rates and times of waiting in line of the first participant 81 in various events. The first action information 81*i* may include information concerning age and sex of the first participant 81.

In this embodiment, for example, the first participant 81 performs registration when participating in the event. Specific recognition information (e.g., an ID) is given to the first participant 81 according to the registration. The first participant 81 holds the held object 30 (cheering goods). The held object 30 is associated with the recognition information. The first sensor 31 (e.g., an acceleration sensor) is provided in the held object 30. The first memory 31*d* is also provided in the held object 30. The first participant 81 performs an action for cheering the performer 85 of the event. The first participant 81 performs, for example, an action for observing manners in the event. In addition to such actions, a goods purchase history by a POS is acquired as the first action information 81*i*. The first action information 81*i* is evaluated. A result the evaluation is converted into parameters. On the other hand, a plurality of services associated with the parameters are prepared by the management organization of the event. The plurality of services include, for example, other events in which the first participant 81 can participate, accessible other Web services, and obtainable contents. The evaluation result of the first action information 81*i* is collated with the plurality of services associated with the parameters. The collation is performed by, for example, an information processing device on a cloud. For example, an evaluation of actions including unconscious actions of the first participant 81 is performed. For example, restriction of access to contents is changed on the basis of a result of the evaluation.

According to this embodiment, it is possible to provide the service providing system that can provide a service more suitable for participants participating in an event to the participants

Fourth Embodiment

Figure 13:
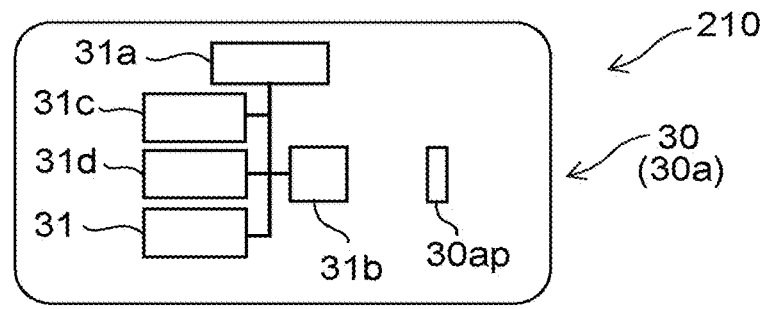
FIG. 13 is a schematic diagram illustrating a service providing device according to a fourth embodiment.

FIG. 13 is a schematic diagram illustrating a service providing device according to a fourth embodiment.

A service providing device 210 according to this embodiment is used in, for example, the service providing system 110 according to the embodiment.

As shown in FIG. 13, the service providing device 210 includes the first sensor 31 and the first communication unit 31*c*.

The first sensor 31 is held by the first participant 81 participating in the event. In this example, the first sensor 31 is provided in the held object 30 (in this example, the light emitting device 30*a*). The first sensor 31 detects at least any one of a movement of the first body 81*b* of the first participant 81, a state of the first body 81*b*, and voice of the first participant 81 at the time when the first participant 81 participates in the event.

The first communication unit 31*c* transmits a result of the detection. Further, the first communication unit 31*c* receives the first service 81*s* based on the result and provides the first service 81*s* to the first participant 81.

The first service 81*s* received by the first communication unit 31*c* may be, for example, a password of an authority for accessing contents. For example, an application program stored in the memory 31*d* may be started according to information concerning the first service 81*s* received by the first communication unit 31*c*.

According this embodiment, it is possible to provide a service providing device that can provide a service suitable for participants participating in an event to the participants.

The service providing device 210 may further include at least any one of the battery 31a, the first processing device 31b, and the first memory 31d.

A form of the service providing device 210 may have, for example, a form of any held object 30 explained with reference to FIG. 9A to FIG. 9C.

Fifth Embodiment

Figure 14:
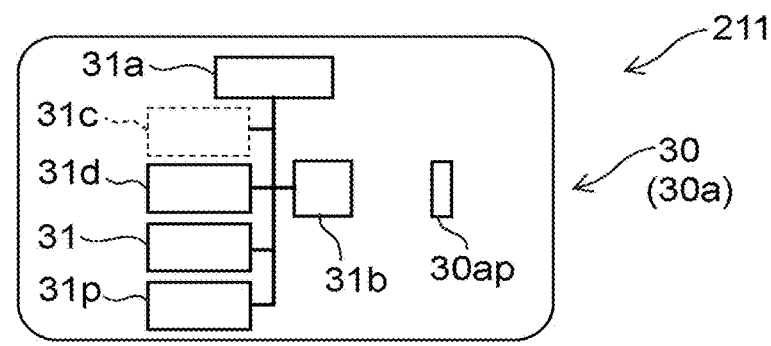
FIG. 14 is a schematic diagram illustrating a service providing device according to a fifth embodiment.

FIG. 14 is a schematic diagram illustrating a service providing device according to a fifth embodiment.

A service providing device 211 according to this embodiment is used in, for example, the service providing system 110 according to the embodiment.

As shown in FIG. 14, the service providing device 211 includes, for example, the first sensor 31 and a providing unit 31p.

The first sensor 31 is held by the first participant 81 participating in an event. In this example, the first sensor 31 is provided in the held object 30 (the light emitting device 30a). The first sensor 31 detects at least any one of a movement of the first body 81b of the first participant 81, a state of the first body 81b, and voice of the first participant 81 at the time when the first participant 81 participates in the event.

The providing unit 31p provides the first service 81s based on a result of the detection to the first participant 81. The providing unit 31p may be, for example, a display unit. The providing unit 31p may store information including the first service 81s. The first participant 81 may provide information including the first service 81s stored in the providing unit 31p to another information device and receive the first service 81s.

In this example, the first memory 31d is provided in the service providing device 211. Various contents are stored in the first memory 31d. The providing unit 31p provides at least any one of a plurality of contents stored in the first memory 31d to the first participant 81 as the first service 81s on the basis of a result of the detection.

The first memory 31d is, for example, a recording medium having a large capacity. Large-volume contents are recorded in the first memory 31d. The first action information 81i of the first participant 81 detected by the first sensor 31 is evaluated in the service providing device 211. For the evaluation, for example, an evaluation program stored in the first memory 31d is used. The evaluation is performed by, for example, the first processing device 31b. For example, viewing restriction for contents is released stepwise on the basis of a result of the evaluation.

For example, cheering goods are distributed in an event (e.g., a concert). The distribution is, for example, charged or free of charge. The service providing device 211 includes the cheering goods. The cheering goods are, for example, a held object. Information including at least any one of a photograph, a video, music, voice, a discount ticket, and an advertisement is stored in the cheering goods. These kinds of information are provided from a management organization of the event. The information includes, for example, a plurality of contents. For example, access restriction is provided for several contents. At first, the first participant 81 cannot access the several contents. A motion performed by the first participant 81 using the cheering goods is detected by the first sensor 31. A result of the detection is the first action information 81i. Note that the detection result is evaluated and the access restriction for the contents is released according to the detection result.

In this example, the first action information 81i is acquired and the first service 81s is provided by processing in the service providing device 211. Since communication with other devices can be omitted, it is possible to perform high-speed processing. Further, an increase in a communication capacity in an event venue is suppressed and a load on operation of the event is reduced. In this case, the first communication unit 31c may be omitted.

The service providing device 211 includes, for example, a providing unit 31p. The providing unit 31p provides an access permission signal to the first participant 81 on the basis of the first action information 81i. The first action information 81i includes at least any one of a movement of the first body 81b of the first participant 81, a state of the first body 81b, and voice of the first participant 81 at the time when the first participant 81 participates in the event. The first action information 81i is detected from, for example, image data of the first participant 81 and voice data of the first participant 81. The access permission signal is a signal concerning access permission to information concerning the first service 81s. The information concerning the first service 81s is stored in, in an access restricted state, the storing unit (e.g., the first memory 31d) provided in the held object 30 held by the first participant 81 in the event.

Sixth Embodiment

Figure 15:
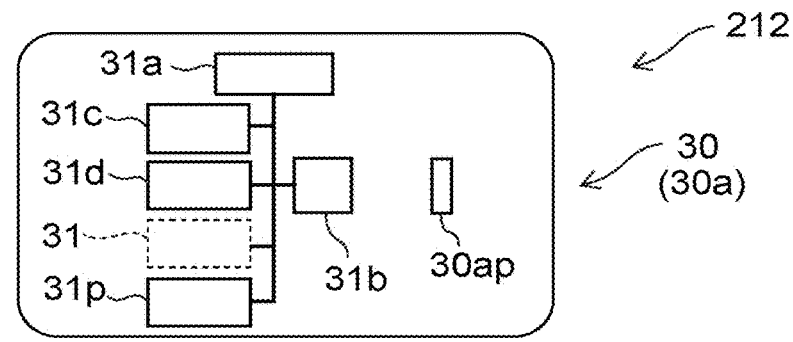
FIG. 15 is a schematic diagram illustrating a service providing device according to a sixth embodiment.

FIG. 15 is a schematic diagram illustrating a service providing device according to a sixth embodiment.

A service providing device 212 according to this embodiment is used in, for example, the service providing systems 110 and 111 according to the embodiment.

As shown in FIG. 15, the service providing device 212 includes the providing unit 31p. The providing unit 31p provides the first service 81s to the first participant 81 on the basis of the first action information 81i of the first participant 81.

The first action information 81i includes at least any one of a movement of the first body 81b of the first participant 81, a state of the first body 81b, and voice of the first participant 81 at the time when the first participant 81 participates in the event. The first action information 81i is information concerning the first participant 81 detected from image data of the first participant 81 and voice data of the first participant 81. The first action information 81i is acquired by, for example, at least either one of the imaging unit 11 and the microphone 12. The imaging unit 11 and the microphone 12 are provided in, for example, a venue of the event.

In this example, the service providing device 212 includes the first communication unit 31c. The acquired first action information 81i is acquired by the first communication unit 31c. The first action information 81i acquired by the first communication unit 31c is evaluated in the service providing device 212. The first service 81s is provided by the providing unit 31p on the basis of a result of the evaluation.

The service providing device 212 includes cheering goods. Information including at least any one of a photograph, a video, music, sound, a discount ticket, and an advertisement is stored in the cheering goods. The information includes, for example, a plurality of contents. For example, access restriction is provided in several contents. A motion of the first participant 81i in the event is detected by the imaging unit 11, the microphone 12, or the like. A result of the detection is evaluated. The access restriction for the contents is released according to the detection result.

In the service providing device 212, for example, it is possible to access any one of the plurality of contents according to information obtained by at least either one of a wireless communication system and a digital signage provided in the venue of the event.

In this embodiment, it is possible to provide a service matching each of a plurality of participants without performing large-capacity communication by a large number of participants.

In the service providing device 212, the evaluation of the first action information 81i may be performed separately from the service providing device 212. Information concerning a result of the evaluation may be transmitted to the service providing device 212.

In the service providing device 212, the plurality of contents serving as the first service 81s may be provided separately from the service providing device 212. The service providing device 212 may obtain, for example, the separately provided plurality of contents via wired or wireless any communication system.

In the service providing device 212, access to any one of the plurality of contents may be enabled according to information obtained by a system such as a POS or the Internet.

The service providing device 212 may be a portable information terminal device. For example, a plurality of contents (an image, a video, music, etc.) are saved in the information terminal device irrespective of selection by the first participant 81. For example, a heartbeat of a user is detected by a wearable device for performing physical condition management. Access to any one of the plurality of contents is enabled according to a result of the detection. In this example, it is possible to provide a service matching each user without imposing a load on a communication infrastructure system.

For example, a state of a human or an animal is detected by a state sensor. The state sensor includes, for example, at least nay one of an acceleration sensor (e.g., the first sensor 31), the imaging unit 11, the microphone 12, and a position information sensor. The position information sensor includes, for example, a satellite positioning system (including, for example, a GPS). The position information sensor includes, for example, a positioning system that makes use of a wireless communication device. The state sensor may include a sensor that detects a physical state. The sensor that detects a physical condition measures at least any one of a body temperature, a heartbeat, a blood pressure, and perspiration.

A service corresponding to a result of the state sensor is provided. The service includes enabling access to a plurality of data stepwise. The access to the plurality of data includes, for example, provision of any one of the plurality of contents. The access to the plurality of data includes release of access restriction for the plurality of contents.

The plurality of contents include, for example, at least any one of an image, a video, music, and sound. The plurality of data include, for example, a password, a personal identification number, and a barcode. The plurality of data include information concerning at least either one of an Internet service and application software. The plurality of data include software for operating contents.

The plurality of data is stored in, for example, a storage medium provided in an information device (a portable terminal device, a personal computer, etc.). The plurality of data may be stored in a storage medium set on the Internet.

The storage media are stored in, for example, a disk medium (including, for example, a hard disk, a DVD, and a CD) or a semiconductor memory (e.g., a nonvolatile semiconductor storage device).

The embodiment includes enabling the data recorded in the storage medium stepwise according to a result of the state sensor.

In the embodiment, for example, when the user is moving in a place including at least any one of a public facility, a commercial facility, a shopping mall, an amusement park, and a street, selection of information is performed according to items registered beforehand in a wearable terminal that acquires information distributed from a short-range wireless terminal (a beacon) set in the place. At this point, for example, personal information is unnecessary in the wearable terminal. For example, the set short-range wireless terminal delivers information to the user only concerning the registered items.

For example, in shopping, a moving route of the user or movement of commodities is measured by an image analyzing device and a wireless communication device. The image analyzing device and the wireless communication device are incorporated in, for example, a cart (including a basket) used by the user. The image analyzing device and the wireless communication device may be set in a facility. For example, a purchase rate estimated from at least either one of consideration for people around the user during congestion and carry-in and out of commodities is measured. At this point in time, for example, registration of personal information is not performed. The purchase rate is treated as information concerning the cart. For example, a coupon corresponding to the purchase rate is issued.

There is a system that provides various services to the user. For example, it is desired to provide an appropriate service to participants participating in an event such as a concert or sports. According to the embodiment, it is possible to provide the service providing system and the service providing device that can provide a service more suitable for participants participating in an event to the participants.

Seventh Embodiment

A seventh embodiment relates to a data constructing method for accumulating data concerning a deep emotion experience UX. The seventh embodiment relates to, for example, an example of generation of the "persona" explained concerning the first embodiment.

The seventh embodiment provides a convenient data constructing method. According to the seventh embodiment, in the data constructing method, a nickname is acquired and first set information is saved in association with the nickname. The first set information includes first service recognition information of a first service provided to a user corresponding to the nickname and first action information performed concerning the first service by the user.

Figure 16:
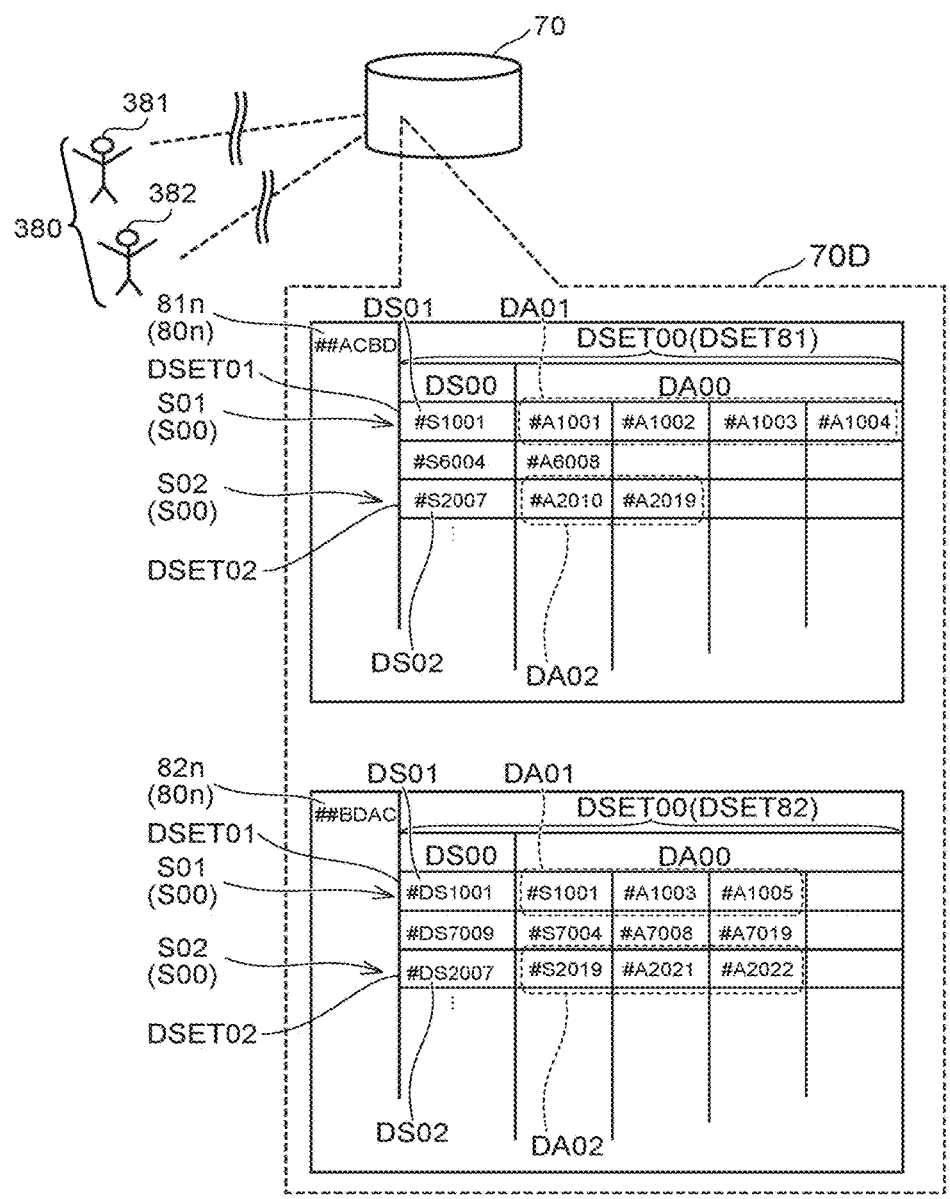
FIG. 16 is a schematic diagram illustrating the data constructing method according to the seventh embodiment.

FIG. 16 is a schematic diagram illustrating the data constructing method according to the seventh embodiment.

As shown in FIG. 16, in the data constructing method according to the seventh embodiment, for example, data 70D is constructed concerning each of the plurality of users 380 (e.g., the first user 381 and the second user 382).

The data 70D is saved in, for example, a storing unit 70. The storing unit 70 is provided in any place on the Internet. The storing unit 70 may be provided in, for example, a cloud server. The storing unit 70 may include a plurality of portions. The plurality of portions may be provided to be spatially separated from one another. The storing unit 70 can be accessed by a wireless or wired method.

The data 70D is constructed to correspond to a nickname 80n of each of the plurality of users 380. Each of the plurality of users 380 is associated with each of the plurality of nicknames 80n. For example, the first user 381 is associated with a first nickname 81n. The second user 382 is associated with a second nickname 82n.

In an example shown in FIG. 16, the first nickname 81n is represented by a character string "##ACBD". The second nickname 82n is represented by a character string "##BDAC". For example, the nickname 80n is decided by the user 380. A character string of the nickname 80n is optional. For example, a password or the like may be combined with the nickname 80n. Consequently, when the same nickname 80n is used in the plurality of users 380, it is possible to identify different users 380.

The nickname 80n is different from a real name of the user 380. For example, the nickname 80n can be set such that the user 380 cannot be specified from the nickname 80n. The nickname 80n does not include, for example, personal information of the user 380. The nickname 80n is not associated with, for example, personal information of the user 380. The nickname 80n can be set not to be associated with, for example, a mail address from which the user 380 can be specified. The nickname 80n can be set not to be associated with, for example, a credit card from which the individual can be specified.

Various services S00 is provided to the user 380. The service S00 is, for example, an event. The service S00 may include, for example, guidance to participation in the event. The user 380 acts in relation to the service S00. For example, the user 380 participates in the event to which the user 380 is guided. For example, the user 380 purchases a commodity related to the event to which the user 380 is guided.

The service S00 may be provided to, for example, the user 380 by an implementer who implements the data constructing method according to the seventh embodiment. For example, application software (a management application) is provided to the user 380 by the implementer who implements the data constructing method according to the seventh embodiment. The service S00 may be provided to the user 380 by the application software.

Alternatively, the service S00 may be provided to the user 380 by, for example, an entity different from the implementer who implements the data constructing method according to the seventh embodiment. For example, application software (a management application) is provided to the user 380 by the implementer who implements the data constructing method according to the seventh embodiment. Various kinds of information concerning the service S00 provided to the user 380 by the entity different from the implementer who implements the data constructing method according to the seventh embodiment may be received from and transmitted to the user 380 by the application software.

For example, a plurality of services S00 (e.g., a first service S01 and a second service S01) are supplied to the user 380. Data for specifying the service S00 (service recognition information DS00) is given to correspond to each of the plurality of services S00. On the other hand, data (action information DA00) is given to correspond to an action of the user 380.

For example, the first service S01 is provided to the first user 381. The first service S01 is, for example, a first event (e.g., a first concert). The first service S01 has first service recognition information DS01. In this example, the first service recognition information DS01 is a character string (data) of "#S001". The character string can be set according to any rules.

Further, the second service S02 is provided to the first user 381. The second service S02 is, for example, a second event (e.g., a second concert). The second service S02 has second service recognition information DS02. In this example, the second service recognition information DS02 is character string (data) "#S2007". The character string can also be set according to the any rules.

In this way, an ID number (the service recognition information DS00, for example, an event number) is provided to correspond to each of the plurality of services S00 (e.g., an event).

The first user 381 participates in the first service S01 (the first concert, which is the first event). An action of application to participation is performed by the first user 381. For example, an admission ticket is purchased according to the action. Further, in relation to the first service S01 (the first concert), the first user 381 purchases an article (e.g., the held object 30 explained with reference to FIG. 10) used during the first concert. The article corresponds to the goods 300. The article is, for example, a light emitting device for cheering used in the first concert. Further, the first user 381 purchases, for example, software of music played in the first concert. The first user 381 performs an action of cheering during the first concert.

For example, the action information DA00 is given to each of such actions of the first user 381. For example, first action information DA01 is given to the action taken by the first user 381 concerning the first service S01. A plurality of kinds of first action information DA01 may be provided.

In the example shown in FIG. 16, the first action information DA01 of the first user 381 concerning the first service S01 includes character strings (data) such as "#A1001", "#A1002", "#A1003", and "#A1004". For example, the character string "#A1001" corresponds to "the application to participation" (the purchase of an admission ticket) explained above. For example, the character string "#A1002" corresponds to "the purchase of an article" explained above. For example, the character string "#A1003" corresponds to "the purchase of software or the like" explained above. For example, the character strings of "#A1004" and the like include "a degree of an action of cheering". An example of "the degree of an action of cheering" is explained below. In this way, the first action information DA01 includes the various kinds of information concerning the actions performed by the first user 381 concerning the first service S01.

For example, the first user 381 notifies other people concerning the second service S02 (the second concert, which is the second event). Further, the first user 381 transmits an impression concerning the second service S02 in relation to the first service S01 (the second concert).

For example, second action information DA02 is given to an action performed by the first user 381 concerning the second service S02. In this case, as in the case explained above, a plurality of kinds of second action information DA02 are provided.

In the example shown in FIG. 16, the second action information DA02 of the first user 381 concerning the second service S02 includes character strings (data) such as "#A2010" and "#A2019". For example, the character string "#A2010" corresponds to "the notification to other people" explained above. For example, the character string "#A2019" corresponds to "the transmission of an impression" explained above. In this way, the second action information DA01 includes the various kinds of information concerning the actions performed by the first user 381 concerning the second service.

In the seventh embodiment, a set of the data for specifying the service S00 (the service recognition information DS00) and the data corresponding to the action of the user 380 corresponding to the nickname 80n (the action information DA00) is treated as set information DSET00. The set information DSET00 corresponds to the plurality of services S00.

In the seventh embodiment, the set information DSET00 is peculiar to one nickname 80n. That is, the set information DSET00 is peculiar to each of the plurality of users 380. For example, set information DSET81 peculiar to the first nickname 81n is associated with the first nickname 81n. The set information DSET81 peculiar to the first nickname 81n includes, for example, first set information DSET01 concerning the first service S01 and second set information DSET02 concerning the second service S02.

In this way, the plurality of services S00 are provided to each of the users 380. In each of the plurality of users 380, information related to the service S00 is saved. The saved information (data) includes information for specifying the service S00 (the service recognition information DS00) and information concerning the action of the user 380 relating to the service S00 (the action information DA00). The saved information (data) is saved in association with the nickname 80n of the user 380. Consequently, the saved information (data) includes a history of the action relating to the service S00 of the user 380 even if the individual user 380 is not specified. The information concerning the history of the action can be not associated with the information for specifying the individual. Therefore, security management is easy. A use range of data is conveniently expanded.

For example, the set information DSET81 corresponding to the first user 381 is saved in association with the first nickname 81n corresponding to the first user 381. The saved information (data) includes a history of the action relating to the service S00 of the first user 381 even if the individual first user 381 is not specified. Consequently, it is possible to grasp a taste of a service corresponding to the first user 381 (i.e., the first nickname 81n).

In the seventh embodiment, the set information DSET00 is peculiar to each of the plurality of users 380. For example, the second nickname 82n is provided to correspond to the second user 382. The set information DSET81 peculiar to the second nickname 82n is associated with the second nickname 82n. The set information DSET82 corresponding to the second nickname 82n may include, for example, the first set information DSET01 concerning the first service S01 and the second set information DSET02 concerning the second service S02. For example, the first set information DSET01 concerning the first service S01 corresponding to the second nickname 82n may be different from the first set information DSET01 concerning the first service S01 corresponding to the first nickname 81n. For example, the second set information DSET02 concerning the second service S02 corresponding to the second nickname 82n may be different from the second set information DEST02 concerning the second service S02 corresponding to the first nickname 81n.

As explained above, in the seventh embodiment, in the data constructing method, the nickname 80n (the first nickname 81n, etc.) is acquired. The first set information DSET01 including the first service recognition information DS01 of the first service S01 provided to the user 380 (the first user 381) corresponding to the nickname 80n and the first action information DA01 of the first action performed concerning the first service S01 by the user 380 (the first user 381) is saved in association with the nickname 80n (the first nickname 81n). The saving is performed in, for example, the storing unit 70.

Further, in the data constructing direction according to the seventh embodiment, the second set information DSET02 including the second service recognition information DS02 of the second service S02 provided to the user 380 (the first user 381) and the second action information DA02 of the second action performed concerning the second service S02 by the user 380 (the first user 381) is saved in association with the nickname 80n (the first nickname 81n). The saving is also performed in, for example, storing unit 70.

Data of actions relating to the plurality of services S00 is accumulated to correspond to the nickname 80n provided in each of the users 380. The accumulated data accurately represents a taste of the user 380. Even in a state in which the user 380 is not specified, data relating to the taste of the user 380 is efficiently obtained.

By using such data, it is possible to grasp a tendency of a taste of a target. It is possible to provide an appropriate service according to the tendency of the taste. Further, the data is associated with the nickname 80n rather than an individual name of the user 380. Such data can be not associated with information for specifying the individual user 380. Therefore, security management is easy. A use range of data is conveniently expanded.

As explained above, in the data constructing method according to the seventh embodiment, the nickname 80n is acquired. A plurality of kinds of set information DSET00 concerning the user 380 corresponding to the nickname 80n is saved in association with the nickname 80n. Each of the plurality of kinds of set information DSET00 includes each of a plurality of kinds of service recognition information DS00 and each of a plurality of kinds of action information DA00. Each of the plurality of kinds of service recognition information DS00 is provided in each of the plurality of services S00 provided to the user 380 corresponding to the nickname 80n. Each of the plurality of kinds of action information DA00 relates to each of a plurality of actions performed concerning the plurality of services S00 by the user.

By accumulating the plurality of kinds of set information DSET00 to correspond to the plurality of services S00, information concerning a taste corresponding to the nickname 80n is accumulated. That is, by accumulating the plurality of kinds of set information DSET00 to correspond to the plurality of services S00, persona data is accumulated, for example, on a cloud. The persona data is associated with the nickname 80n corresponding to the user 380. For example, a persona corresponding to each of the plurality of users 380 is generated on a platform. The personal can be set such that the individual is not specified. The persona efficiently reflects a taste of each of the users 380.

In the seventh embodiment, the user 380 performs exchange of data with the storing unit 70, for example, through the Internet line. For example, a server is provided on the cloud. It is possible to perform communication with the storing unit 70 through the server.

For example, application software (a management application) is provided to the user 380 by the implementer who implements the data constructing method. For example, user 380 can access a predetermined portal site according to execution of the application software. For example, a predetermined input screen is provided on the portal site. Each of the users 380 registers the nickname 80*n* with the input screen. For example, a password is set together with the nickname 80*n*.

For example, a place where data corresponding to each of the users 380 is saved (a memory region specified on software) is set according to the registration of the nickname 80*n*. The plurality of kinds of set information DSET00 can be saved in the memory region.

The action information DA00 may include actions of a user before and after the event. The action information DA00 includes, for example, actions such as preparation before the event and selection, purchase, and preparatory adjustment of participation certificates, articles (goods) for performing cheering, and the like. Specifically, for example, when the user registers a nickname common to a system in a sales site of cheering goods, connection of data is carried out in the system. At this point, click operation, tap operation, or the like in a selection process of a component, a computer program, or a service proposed to the user is recorded. A finally determined combination of these kinds of operation is recorded. When there is a real community site and a communication site on the Internet that the user is permitted to use using the same nickname, a model and the like laid open to the public under the permission of the user in such community sites may be associated with the community sites. The model includes, for example, alternation of a computer program by the user and alternation of hardware. At that point, a new action data number is registered anew in the sites.

Thereafter, similarly, concerning a real service and a service on the Internet, the same nickname is used by the user. When the user users the services in which the same nickname is used, connection of action data is carried out on the basis of data set in advance. Intensity of connection to a connection destination of data is performed by manual setting by an administrator or an automated computer program.

The action information DA00 can include, for example, an act of talking with friends before the event or talking in a community, communication means with the friends or the community, content of the talk, and a history of operation concerning goods.

The action information DA00 can include, for example, an act of confirming data after the event, an act of accessing the community, a purchase action, viewing of related photographs moving images, sound, and text, viewing of an advertisement, download of a computer program, participation in a game relating to the event, play content of the game, and information concerning the next event. Further, the action information DA00 may include, for example, communication content concerning the event, an active remark, a supporting action, a claim, a review, an offensive remark to others, and an act that the user passively receives.

The connection of the action data is carried out using tags or keywords added to contents beforehand. The connection of the action data may be manually set by the administrator or may be automatically set using an image analysis, a voice analysis, a text analysis, or the like by the computer program. Rules of the connection of the data are not changed during a service period.

In the seventh embodiment, the service recognition information DS00 (e.g., the first service recognition information DS01 and the second service recognition information DS02) may be input by the user 380. For example, an input screen associated with the nickname 80*n* corresponding to the user 380 is provided according to execution of application software.

The user 380 inputs, for example, a name and an identification number of the service S00 (e.g., an event) to the input screen. The user 380 inputs an identification number and the like corresponding to an action carried out concerning the service S00 (e.g., the event). The user 380 inputs, for example, identification number of a purchased article or the like. The input may include input of a name, a sign, a number, and the like. The input may include, for example, input by a barcode, a two-dimensional code, or the like. The input includes, for example, input by a memory element or the like provided in an article or the like. The memory element is capable of recording information according to, for example, at least any one of electric, magnetic, and optical methods. The identification information of the purchased article or the like may be input using such a memory element.

In this way, for example, at least either one of the first service recognition information DS01 and the first action information DA01 is input by the user 380. For example, at least either one of the second service recognition information DS02 and the second action information DA02 is input by the user 380.

When the user 380 purchases an article relating to the service S00 (the event, etc.), the input by the user 380 may be performed according to transmission of a permission signal associated with a purchase action of the article. For example, when the user 380 purchases an article, an inquiry is performed on the basis of information concerning the purchase. The user 380 is inquired whether transmission of information indicating the purchase of the article to the server associated with the data constructing method according to the seventh embodiment is permitted. The inquiry is performed, for example, on a screen in a browser usable by the user 380. The user 380 permits the transmission of the information indicating the purchase and inputs the nickname 80*n* (and the password) corresponding to the user 380. Consequently, the information indicating the purchase is saved in association with the nickname 80*n*.

On the other hand, in the reference example, when the user purchases an article or the like, information indicating the purchase is automatically transmitted and accumulated rather than by input of the user. In this case, personal information (a name, an address, a mail address, credit card information, etc.) used by the user in purchasing the article and the information indicating the purchase are associated. Therefore, advanced security management is necessary concerning the personal information.

On the other hand, in the seventh embodiment, when at least either one of the first service recognition information DS01 and the first action information DA01 is input by the user 380, the input action information (purchase information) is associated with the nickname 80*n*. The input action information can be not associated with the personal information of the user 380. Therefore, security management is easy.

In the data constructing method according to the seventh embodiment, the user 380 may be urged to input at least either one of the first service recognition information DS01 and the first action information DA01. For example, on a screen corresponding to the nickname 80*n* of the user 380, a name and the like of an event corresponding to the first service recognition information DS01 are displayed and an article name (a commodity name) and the like corresponding to the first action information DA01 are displayed. On the screen, "register this article?" or the like is displayed. The user 380 inputs at least either one of the first service recognition information DS01 and the first behavior information DA01 on the basis of this display, whereby the information is saved in association with the nickname 80n. Further, the user 380 selects an input key for permission, whereby at least either one of the first service recognition information DS01 and the first action information DA01 is saved in association with the nickname 80n.

In the seventh embodiment, a configuration may be provided in which the user 380 desires to input at least either one of the first service recognition information DS01 and the first action information DA01.

For example, a score is set according to a type of the service S00. Further, a score is set according to a type and a degree of an action relating to the service S00. The user 380 desires to increase the score. For example, a figure (a graph, etc.) or the like is provided according to the nickname 80n correspond to the user 380. The figure changes according to the score. The figure is displayed in, for example, a specific place of a portal site. For example, the score may be able to be laid open to the public together with the nickname 80n. The figure corresponding to the score may be laid open to the public together with the nickname 80n. For example, one of the plurality of users 380 can view scores (and figures, etc.) of the nicknames 80n corresponding to the other users 380. The plurality of users 380 desire to obtain predetermined figures. For example, with such a configuration, the user 380 desires to actively input the service S00 and the action information DA00 corresponding to the service S00. With such a configuration, it is possible to efficiently collect various data corresponding to the user 380 (the nickname 80n).

As explained above, in the seventh embodiment, an evaluation result (the score, the figure corresponding to the score, etc.) of the first action information DA01 is displayed. The user 380, who is not the user 380 corresponding to the first action information DA01, may be capable of viewing the display.

For example, an evaluation standard corresponding to the first action information DA01 may be decided. For example, when the first action information DA01 is the service S00 (e.g., a concert), a score of evaluation is given according to a type of an action. The first action information DA01 may be evaluated on the basis of the score (the evaluation standard). The first action information DA01 corresponding to the evaluation standard may be displayed. That is, the first action information DA01 may be evaluated according to weighting.

An example of the service S00 is explained below.

For example, when the user 380 performs purchase of an article, purchase of software, borrowing of the article, borrowing of the software, or the like, the service S00 corresponds to the article or the software.

For example, the user 380 sometimes participates in an event or the like. In this case, the services S00 (the first service S01 and the second service S02, etc.) include, for example, an event (a first event). The users 380 (the first user 381 and the second user 382, etc.) are capable of participating in the event.

The event includes, for example, a concert, a competition, a festival, an exhibition, and a sale. The competition relates to, for example, sports. The competition may include, for example, games (a card game, a board game, and an electronic game). The event may include, for example, a school festival, a wedding ceremony, a travel, and a birthday party. The plurality of users 380 may participate in the event. Various examples of the event are explained below.

For example, a performer is present in the event. The performer includes, for example, at least any one of a singer, an actor, a dancer, an artist, an athlete, and an executer of a game. The performer may include a producer or a creator relating to the event. The performer includes, for example, a recorded video such as a movie, an artwork, food, and a product. The performer includes another user participating in the event.

In the following explanation, to simplify the explanation, it is assumed that the event is a concert of a singer.

The first user 381 participates in the concert. The first user 381 is a viewer. When the first user 381 participates in the concert, the first user 381 takes an action for cheering the performer (e.g., a singer). For example, the first user 381 performs a hand-clap, emits voice, swings the body, and dances according to a state of the performer. In the case of this example, the state of the performer includes a state of at least any one of a song, music, and a dance of the performer. The state of the performer may include at least any state of illumination, gas emission, and vibration.

For example, the first user 381 sometimes holds an article such as a penlight that emits light. An example of the article is explained below. The first user 381 sometimes moves the article according to the song and the dance of the performer. Such an action of the first user 381 is included in the first action information DA01.

For example, the first action information DA01 is evaluated. For example, a degree of matching of a movement of the penlight of the first user 381 with a state (a movement, rhythm of music, etc.) of the performer is evaluated. For example, when a result of the evaluation reaches a standard, a high score is given concerning the first action information DA01.

On the other hand, the first user 381 acquires (e.g., purchases) an article related to the first service S01 (a first event, that is, a concert). The first action information DA01 may include information concerning the acquisition of the article. That is, the first action information DA01 may include information concerning the article (article information) concerning the first event acquired by the user 380 (the first user 381).

The article may be held by the first user 381 during the first service S01 (the first event, that is, the concert). An acceleration sensor or the like may be provided in the article. A movement of the article is detected by the sensor. As a result, an action of the first user 381 can be detected.

The article in the seventh embodiment may include, for example, the held object 30 explained concerning the second to sixth embodiments. For example, the article includes at least any one of the light emitting device 30a, the flag-like body 30b, the fan-like body 30c, the cloth-like body 30d, the megaphone 30e, the microphone 30f, the bracelet 30g, the necklace 30h, the watch 30i, the finger ring 30j, the eyeglasses 30k, the clothes 30l, the shoe 30m, the glove 30n, and the cap 30o illustrated in FIG. 9A to FIG. 9C.

The sensor 31 is provided in the articles (e.g., the held object 30). The sensor 31 includes, for example, an acceleration sensor. The sensor 31 detects information (included in the first action information DA01) including a movement of the body of the first user 381. The sensor 31 detects at least any one of acceleration, speed, and a moving direction of at least part of the body of the first user 381. When the sensor 31 includes a microphone, the sensor 31 is included in information (the first action information DA01) including voice of the first user 381.

In the seventh embodiment, the light emitting device 30a used as the article may have the configuration explained with reference to FIG. 10. The first memory 31d stores information concerning a detection result. The first memory 31*d* stores information concerning the operation of the first processing device 31*b*. The first memory 31*d* may store information concerning another service (the service S00 different from the first service S01) provided to the user 380.

As explained above, the article (the held object 30) may include at least any one of a light emitting device, a flag-like body, a fan-like body, a cloth-like body, a megaphone, a microphone, a bracelet, a necklace, a watch, a finger ring, eyeglasses, clothes, a shoe, a glove, a cap, a headphone, an earphone, a hearing aid, and an accessory.

For example, the first action information DA01 includes recognition information of these articles. The first action information DA01 may include information indicating that the first user 381 acquires (e.g., purchases) these articles. The articles and the nickname 80*n* are associated with each other. It does not have to be specified who (an individual) owns these articles.

Further, the first action information DA01 may include information at the time when the user 380 (e.g., the first user 381) participates in the first event (information during participation). The information during participation may include, for example, information concerning at least any one of a movement of the body of the user 380 (e.g., the first user 381), a state of the user 380 (e.g., the first user 381), and voice of the user 380 (e.g., the first user 381).

Further, the article may acquire the information during participation. The acquired information during participation may be input by the user 380. The input is saved in the storing unit 70, for example, via a portal site.

Further, the first action information DA01 may include received information, transmitted information, detected information, and the like concerning the first service S01 (the first event, etc.) of the user 380. The transmitted information may include, for example, points that should be improved concerning the first service S01. An evaluation standard may be provided according to types of these kinds of information. Evaluation based on the evaluation standard may be performed.

In the following explanation, evaluation of action information (e.g., the first action information DA01) may be performed according to, for example, the evaluation items explained with reference to FIG. 12. The first action information DA01 is evaluated, for example, on the basis of the evaluation items. For example, exercise of the first body of the first user 381 detected by the sensor 31 is evaluated. A result of the evaluation is indicated by, for example, a radar chart (see FIG. 12). The evaluation result may be indicated by, at least any one of a graph, a sign, an illustration, a pattern, and an avatar (a human figure or a doll). The evaluation result may be represented by, for example, at least either one of gas and liquid. The evaluation result may be indicated by a change in a configuration of a displayed image (e.g., a change in a frame layout of a cartoon). The evaluation result may be represented by the size and a change in a color of display. As visualized representation of the evaluation result, various representations may be applied for each of events.

The evaluation result may be presented from a device worn on the body of the user, a peripheral device, and direction by a space besides the screen display. The evaluation result may be presented by lighting and flashing of a light source, voice, scent, vibration, stimulus to skin, and a change by taste or a combination of the foregoing.

The evaluation items include, for example, a synchronization degree E1 with the performer. The synchronization degree E1 includes a coincidence degree of timings of an action of the first user 381 and a movement of the performer.

The evaluation items include a synchronization degree E2 with another user (e.g., the second user 382). The synchronization degree E2 includes a coincidence degree of timings of a movement of the first user 381 and a movement of another user (the second user 382) different from the first user 381.

The evaluation items include, for example, a movement completion degree E3. The movement completion degree E3 includes a coincidence degree of a movement (e.g., a dance) of the first user 381 and a movement decided in advance. The movement completion degree E3 may include the magnitude and time of a movement. The magnitude of the movement is the size of a range in which the first body of the first user 381 moves. The time of the movement is the length of time in which the first body of the first user 381 exercises.

For example, data obtained by at least either one of the sensor 31, the imaging unit and the microphone is evaluated on the basis of the evaluation items of the synchronization degree E1 with the performer, the synchronization degree E2 with the other user, and the movement completion degree E3.

The evaluation degrees may include, for example, an enthusiasm degree E4. The enthusiasm degree E4 may include, for example, a concentration degree of the first user 381. For example, data including at least either one of a heart rate and a blood pressure of the first body is evaluated as the evaluation item of the enthusiasm degree E4.

The evaluation items may include, for example, a contribution degree E5. The contribution degree E5 includes evaluation of an action (a remark) for carrying out the event better. For example, the action (including the remark) may include, for example, a spontaneous action of the first user 381. For example, the contribution degree E5 may include an action (including a remark) for praising the event. The contribution degree E5 may include an action (including a remark) for proposing improvement points concerning the event. The contribution degree E5 may include an action (including a remark) for solving a trouble in the event. For example, information concerning an action (including a remark) of the first user 381 in the venue of the event is acquired by the sensor 31, the imaging unit, the microphone, and the like. The acquisition of the information includes acquisition from the Internet such as a Web. Such information is evaluated as data of the contribution degree E5.

The evaluation items may include, for example, a cooperation degree E6. The cooperation degree E6 includes, for example, an observance degree to an instruction related to operation of the event. For example, the instruction concerning the operation includes an instruction for movement in the event venue (including an instruction for entrance and exit, an instruction for a rest, and a seat instruction). The instruction concerning the operation may include, for example, instructions performed before the event is held and after the event is held.

For example, in one example of the seventh embodiment, the acquired first action information DA01 is evaluated on the basis of evaluation items (e.g., the evaluation items explained with reference to FIG. 12). The provided other service S00 may be changed on the basis of a result of the evaluation. The evaluation items include, for example, a first relation degree. The first relation degree includes a correlation between provided information including at least either one of music and a video provided in the event and the first action information DA01. The first relation degree includes, for example, the synchronization degree E1 with the performer.

The evaluation items may include, for example, a second relation degree. The second relation degree includes a correlation between second action information concerning an action relating to the event of the second user 382 participating in the event and the first action information DA01. The second relation degree includes the synchronization degree E2 with the second user 382.

As explained above, in the seventh embodiment, various modifications of the evaluation items are possible.

Information concerning a service used by a user is totalized to provide information suitable for the user. It is desired to construct a database that can be conveniently used. According to the seventh embodiment, it is possible to provide a convenient data construction method.

The seventh embodiment is explained above with reference to the data constructing method. However, the seventh embodiment may be a form of a data constructing program for causing a computer to execute the data constructing method. The data constructing program according to the seventh embodiment includes first to eighth features described below.

According to the first feature, the data constructing program acquires a nickname and saves, in association with the nickname, first set information including first service recognition information of a first service provided to a user corresponding to the nickname and first action information performed concerning the first service by the user.

According to the second feature, in the data constructing program according to the first feature, the data constructing program further saves, in association with the nickname, second set information including second service recognition information of a second service provided to the user and second action information of a second action performed concerning the second service by the user.

According to the third feature, in the data constructing program according to the first or second feature, the first service includes a first event in which the user can participate.

According to the fourth feature, in the data constructing program according to the third feature, the first action information includes article information concerning an article relating to the first service acquired by the user.

According to the fifth feature, in the data constructing program according to the third or fourth feature, the first action information includes information concerning at least any one of a movement of the body of the user, a state of the user, and voice of the user at the time when the user participates in the first event.

According to the sixth feature, in the data constructing program according to any one of the first to fifth features, at least either one of the first service recognition information and the first action information is input by the user.

According to the seventh feature, in the data constructing program according to any one of the first to sixth features, an evaluation result of the first action information is displayed.

According to the eighth feature, in the data constructing program according to any one of the first to seventh features, the nickname does not include personal information of the user.

The seventh embodiment may be a form of a computer-readable recording medium having the data constructing program recorded therein. As the recording medium according to the seventh embodiment, specifically, a CD-ROM (-R/-RW), a magneto-optical disk, a HD (hard disk), a DVD-ROM (-R/-RW/-RAM), an FD (flexible disk), a flash memory, a memory card, a memory stick, other various ROMs and RAMs, and the like can be assumed. The data constructing program for causing the computer to execute the data constructing method according to the seventh embodiment explained above is recorded in the recording medium and distributed, whereby realization of the method is facilitated. The recording medium explained above is mounted on an information processing device such as a computer and the data constructing program is read out by the information processing device or the data constructing program is stored in a storage medium included in the information processing device and read out according to necessity, whereby it is possible to execute the data constructing method according to the seventh embodiment.

The embodiments include, for example, configurations explained below.

(Configuration 1)

A service providing system that accumulates, as first context information linked to identification information of a first user, at least a part of first data detected by a first sensor worn on a body of the first user or provided in a held object of the first user and provides a first service based on a first aggregate of the accumulated first context information to the first user.

(Configuration 2)

The service providing system described in the configuration 1, wherein the service providing system accumulates a plurality of kinds of the first context information, estimates a characteristic of the first user on the basis of the first aggregate of the accumulated plurality of kinds of first context information, and decides the first service on the basis of the characteristic of the first user.

(Configuration 3)

The service providing system described in the configuration 2, wherein the service providing system accumulates, as a plurality of kinds of second context information linked to identification information of a second user, at least a part of a plurality of second data detected by a second sensor worn on a body of the second user or provided in a held object of the second user, estimates a characteristic of the second user on the basis of a second aggregate of the accumulated plurality of kinds of second context information, and, when a difference between the estimated characteristic of the second user and the estimated characteristic of the first user is smaller than a standard, provides a second service based on at least the part of the first data to the second user.

(Configuration 4)

The service providing system described in the configuration 3, wherein the provision of the second service to the second user is performed without including personal information of the first user of the first user.

(Configuration 5)

The service providing system described in any one of the configurations 1 to 4, wherein the first sensor detects at least any one of a movement of the body of the first user, a state of the first user, and voice of the first user at a time when the first user participates in an event.

(Configuration 6)

The service providing system described in the configuration 5, wherein the held object of the first user includes at least any one of a light emitting device, a flag-like body, a fan-like body, a cloth-like body, a megaphone, a microphone, a bracelet, a necklace, a watch, a finger ring, eyeglasses, clothes, a shoe, a glove, a cap, a headphone, an earphone, a hearing aid, an accessory, and a sporting instrument.

(Configuration 7)

The service providing system described in the configuration 5 or 6, wherein the first service includes at least any one of image information concerning the event, video information concerning the event, music information concerning the event, and sound information concerning the event.

(Configuration 8)

The service providing system described in any one of the configurations 5 to 7, wherein the service providing system evaluates the first data on the basis of evaluation items and changes the first service on the basis of a result of the evaluation, the evaluation items include a first relation degree and a second relation degree, the first relation degree includes a correlation between provided information including at least either one of music and a video provided in the event and the first data, and the second relation degree includes a correlation between second data concerning an action relating to the event of a second user participating in the event and the first data.

(Configuration 9)

The service providing system described in any one of the configurations 1 to 8, wherein the service providing system evaluates the first context information on the basis of evaluation items and changes the first service on the basis of a result of the evaluation.

(Configuration 10)

The service providing system described in the configuration 9, wherein the first service includes at least either one of first image information created on the basis of the first context information and second image information created on the basis of the result of the evaluation.

(Configuration 11)

The service providing system described in any one of the configurations 1 to 10, wherein the provision of the first service to the first user includes enabling access by the first user to information provided to the first user.

(Configuration 12)

A service providing device comprising:

a first sensor held by a first participant participating in an event and configured to detect at least any one of a movement of a first body of the first participant, a state of the first body, and voice of the first participant at a time when the first participant participates in the event; and a first communication unit configured to transmit a result of the detection, receive a first service based on the result, and provide the first service to the first participant.

(Configuration 13)

A service providing device comprising:

a first sensor held by a first participant participating in an event and configured to detect at least any one of a movement of a first body of the first participant, a state of the first body, and voice of the first participant at a time when the first participant participates in the event; and a providing unit configured to provide a first service based on a result of the detection to the first participant.

(Configuration 14)

A service providing device comprising a providing unit configured to provide, on the basis of first action information of a first participant including at least any one of a movement of a first body of the first participant, a state of the first body, and voice of the first participant at a time when the first participant participates in an event and detected from image data of the first participant and voice data of the first participant, to the first participant, an access permission signal for information concerning a first service stored in an access restricted state in a storing unit provided in a held object held by the first participant.

(Configuration 15)

A data constructing method comprising:

acquiring a nickname; and saving, in association with the nickname, first set information including first service recognition information of a first service provided to a user corresponding to the nickname and first action information performed concerning the first service by the user.

(Configuration 16)

The data constructing method described in the configuration 15, further comprising saving, in association the nickname, second set information including second service recognition information of a second service provided to the user and second action information of a second action performed concerning the second service by the user.

(Configuration 17)

The data constructing method described in the configuration 15 or 16, wherein the first service includes a first event in which the user can participate.

(Configuration 18)

The data constructing method described in the configuration 17, wherein the first action information includes article information concerning an article relating to the first service acquired by the user.

(Configuration 19)

The data constructing method described in the configuration 17 or 18, wherein the first action information includes information concerning at least any one of a movement of a body of the user, a state of the user, and voice of the user at a time when the user participates in the first event.

(Configuration 20)

The data constructing method described in any one of the configurations 15 to 19, wherein the nickname does not include personal information of the user.

According to the embodiments, it is possible to provide the service providing system, the service providing device, and the data constructing method that can provide more enjoyment.

The embodiments of the invention are explained above with reference to the specific examples. However, the invention is not limited to the specific examples. For example, specific configurations of the elements such as the acquiring unit, the providing unit, the imaging unit, the microphone, the obtaining unit, the sensor, the battery, the processing device, the memory, and the communication device included in the service providing system and the service providing device are included in the scope of the invention as long as those skilled in the art can carry out the invention in the same manner by appropriately selecting the configurations from a publicly known range and obtain the same effects.

A combination of any two or more elements in the specific examples within a technically available range is included in the scope of the invention as long as the combination includes the gist of the invention.

Besides, all service providing systems and all service providing devices that those skilled in the art can change in design as appropriate and implement on the basis of the service providing systems and the service providing devices explained above as the embodiments of the invention also belong to the scope of the invention as long as the service providing systems and the service providing devices include the gist of the invention.

Besides, in the category of the idea of the invention, those skilled in the art can arrive at various alterations and modifications. It is understood that the alternations and the modifications also belong to the scope of the invention.

The several embodiments of the invention are explained above. However, the embodiments are presented as examples and are not intended to limit the scope of the invention. These new embodiments can be implemented in other various forms. Various omissions, substitutions, and changes can be performed without departing from the spirit of the invention. The embodiments and modifications of the embodiments are included in the scope and the gist of the invention and included in the inventions described in claims and the scope of equivalents of the inventions.

REFERENCE SIGNS LIST 10 acquiring unit
11 imaging unit
12 microphone
15 obtaining unit
20 providing unit
30 held object
30a light emitting device
30ap light emitting unit
30aq light guide body
30ar housing
30b flag-like body
30c fan-like body
30d cloth-like body
30e megaphone
30f microphone
30g bracelet
30h necklace
30i watch
30j finger ring
30k eyeglasses
30l clothes
30m shoe
30n glove
30o cap
31 first sensor
31a battery
31b first processing device
31c first communication unit
31d first memory
31p providing unit
40 information terminal device
70 storing unit
70D data
80 user
80n nickname
81 first participant
81b first body
81i first action information
81n first nickname
81s first service
82 second participant
82i second action information
82n second nickname
82s second service
85 performer
110, 111 service providing system
210 to 212 service providing device
300 goods
310 sensing device
321, 322 first event, second event
323, 324 commodity
350 cloud
351 cloud server
360 management application software
361 real UX
362 virtual UX
370 provider
370a authorization
370b service
370c advertisement
370d service
370e business data
370f consumer data
375 special thing
376 application software
377 special application software
380 user
380ID persona
380a consumer data
380d data
381 to 383 first to third user
381ID to 383ID first to third ID
385 performer
391 goods seller
392 community operator
392a social network service
392b contents and an article
392c advertisement
392d official approval
392e business data
392f consumer data
393 advertiser
394 event organizer
395 business operator
395a synthesis data
395b mage analysis
395c data analysis
395d sound synthesis
510 service providing system
DA00 action information
DA01, DA02 first, second action information
DS00 service recognition information
DS01, DS02 service recognition information
DSET00 set information
DSET01, DSET02 first, second set information
DSET81, DSET82 set information
E1 synchronization degree
E2 synchronization degree
E3 completion degree
E4 enthusiasm degree
E5 contribution degree
D6 cooperation degree
EX1 to EX3 first to third example
MT motivation
S00 service
S01, S02 first, second service
S110 to S130 step
ST01 to ST04 step
UX 361 real UX
UX 362 virtual UX
t time
t1 to t7 first to seventh time

The invention claimed is:
1. A service providing system comprising:
a server configured to
accumulate, as first context information linked to identification information of a first user, at least a part of first data detected by a first sensor worn on a body of the first user or provided in a held object of the first user, provide a first service based on a first aggregate of the accumulated first context information to the first user, accumulate a plurality of kinds of the first context information, estimate a characteristic of the first user based on the first aggregate of the accumulated plurality of kinds of first context information, decide the first service based on the characteristic of the first user, accumulate, as a plurality of kinds of second context information linked to identification information of a second user, at least a part of a plurality of second data detected by a second sensor worn on a body of the second user or provided in a held object of the second user, estimate a characteristic of the second user based on a second aggregate of the accumulated plurality of kinds of second context information, determine a difference between the estimated characteristic of the second user and the estimated characteristic of the first user, and in response to the determination that the difference is less than a standard, provide a second service based on at least the part of the first data to the second user.

2. The system according to claim 1, wherein the provision of the second service to the second user is performed without including personal information of the first user of the first user.

3. The system according to claim 1, wherein the first sensor detects at least any one of a movement of the body of the first user, a state of the first user, and voice of the first user at a time when the first user participates in an event.

4. The system according to claim 3, wherein the held object of the first user includes at least any one of a light emitting device, a flag-like body, a fan-like body, a cloth-like body, a megaphone, a microphone, a bracelet, a necklace, a watch, a finger ring, eyeglasses, clothes, a shoe, a glove, a cap, a headphone, an earphone, a hearing aid, an accessory, and a sporting instrument.

5. The system according to claim 3, wherein the first service includes at least any one of
image information concerning the event,
video information concerning the event,
music information concerning the event, and
sound information concerning the event.

6. The system according to claim 3, wherein
the service providing system evaluates the first data on the basis of evaluation items and changes the first service on the basis of a result of the evaluation,
the evaluation items include a first relation degree and a second relation degree,
the first relation degree includes a correlation between provided information including at least either one of music and a video provided in the event and the first data, and
the second relation degree includes a correlation between second data concerning an action relating to the event of a second user participating in the event and the first data.

7. The system according to claim 1, wherein the service providing system evaluates the first context information on the basis of evaluation items and changes the first service on the basis of a result of the evaluation.

8. The system according to claim 7, wherein the first service includes at least either one of first image information created on the basis of the first context information and second image information created on the basis of the result of the evaluation.

9. The system according to claim 1, wherein the provision of the first service to the first user includes enabling access by the first user to information provided to the first user.

10. A service providing device comprising:
a first sensor held by a first participant participating in an event and configured to detect at least any one of a movement of a first body of the first participant, a state of the first body, and voice of the first participant at a time when the first participant participates in the event; and
circuitry configured to
transmit a result of the detection,
receive a first service based on the result, and
provide the first service to the first participant, wherein the first service is provided based on a first aggregate of accumulated first context information of the first participant,
wherein the first aggregate of the accumulated first context information is used to estimate a characteristic of the first participant, the estimated characteristic of the first participant being compared to an estimated characteristic of a second participant, and in response to a determination that a difference between the estimated characteristic of the first participant and the estimated characteristic of the second participant is less than a standard, a second service is provided to the second participant.

11. A service providing device comprising:
a first sensor held by a first participant participating in an event and configured to detect at least any one of a movement of a first body of the first participant, a state of the first body, and voice of the first participant at a time when the first participant participates in the event; and
circuitry configured to
provide a first service based on a result of the detection to the first participant wherein the first service is provided based on a first aggregate of accumulated first context information of the first participant,
wherein the first aggregate of the accumulated first context information is used to estimate a characteristic of the first participant, the estimated characteristic of the first participant being compared to an estimated characteristic of a second participant, and in response to a determination that a difference between the estimated characteristic of the first participant and the estimated characteristic of the second participant is less than a standard, a second service is provided to the second participant.

12. A service providing device comprising
circuitry configured to
provide, on the basis of first action information of a first participant including at least any one of a movement of a first body of the first participant, a state of the first body, and voice of the first participant at a time when the first participant participates in an event and detected from image data of the first participant and sound data of the first participant, to the first participant, an access permission signal for information concerning a first service stored in an access restricted state in a memory provided in a held object held by the first participant, wherein the first service is provided based on a first aggregate of accumulated first context information of the first participant, wherein the first aggregate of the accumulated first context information is used to estimate a characteristic of the first participant, the estimated characteristic of the first participant being compared to an estimated characteristic of a second participant, and in response to a determination that a difference between the estimated characteristic of the first participant and the estimated characteristic of the second participant is less than a standard, a second service is provided to the second participant.

13. A data constructing method comprising:

acquiring a nickname; and saving, in association with the nickname, first set information including first service recognition information of a first service provided to a first user corresponding to the nickname and first action information performed concerning the first service by the first user, wherein the first service is provided based on a first aggregate of accumulated first context information of the first user, wherein the first aggregate of the accumulated first context information is used to estimate a characteristic of the first user, the estimated characteristic of the first user being compared to an estimated characteristic of a second user, and in response to a determination that a difference between the estimated characteristic of the first user and the estimated characteristic of the second user is less than a standard, a second service is provided to the second participant.

14. The method according to claim 13, further comprising saving, in association the nickname, second set information including second service recognition information of a second service provided to the user and second action information of a second action performed concerning the second service by the user.

15. The method according to claim 13, wherein the first service includes a first event in which the user can participate.

16. The method according to claim 15, wherein the first action information includes article information concerning an article relating to the first service acquired by the user.

17. The method according to claim 15, wherein the first action information includes information concerning at least any one of a movement of a body of the user, a state of the user, and voice of the user at a time when the user participates in the first event.

18. The method according to claim 13, wherein the nickname does not include personal information of the user.

* * * * *